(12) United States Patent
Urata et al.

(10) Patent No.: US 6,265,620 B1
(45) Date of Patent: Jul. 24, 2001

(54) PROCESS FOR PRODUCING ALDEHYDES

(75) Inventors: Hisao Urata; Yasuhiro Wada, both of Yokohama (JP)

(73) Assignee: Mitsubishi Chemical Corporation, Tokyo (JP)

(*) Notice: Subject to any disclaimer, the term of this patent is extended or adjusted under 35 U.S.C. 154(b) by 0 days.

(21) Appl. No.: 09/381,629

(22) PCT Filed: Mar. 26, 1998

(86) PCT No.: PCT/JP98/01362

§ 371 Date: Sep. 27, 1999

§ 102(e) Date: Sep. 27, 1999

(87) PCT Pub. No.: WO98/43935

PCT Pub. Date: Oct. 8, 1998

(30) Foreign Application Priority Data

Mar. 27, 1997 (JP) .................................................. 9-075530
Mar. 27, 1997 (JP) .................................................. 9-075536

(51) Int. Cl.$^7$ .................................................. C07C 45/50
(52) U.S. Cl. .................................................. 568/454; 568/451
(58) Field of Search .................................................. 568/451, 456

(56) References Cited

U.S. PATENT DOCUMENTS 4,400,547 * 8/1983 Dawes et al. ......................... 568/454
5,712,403 * 1/1998 Sato et al. ............................. 556/19

* cited by examiner

Primary Examiner—Sreeni Padmanabhan
(74) Attorney, Agent, or Firm—Oblon, Spivak, McClelland, Maier & Neustadt, P.C.

(57) ABSTRACT

Aldehydes are produced by reacting an olefinic compound with carbon monoxide and hydrogen in the presence of a catalyst containing a metal of Group 8 to 10 and a phosphonite compound as a trivalent organic phosphorus compound.

38 Claims, No Drawings

PROCESS FOR PRODUCING ALDEHYDES

This is the U.S. National Stage Application of PCT/JP98/01362 filed Mar. 26, 1998.

BACKGROUND OF THE INVENTION

1. Technical Field

The present invention relates to a method for producing aldehydes. In particular, the present invention relates to a method for producing aldehydes by subjecting an olefinic compound to a hydroformylation reaction.

2. Background Art

A reaction which comprises reacting an olefinic compound with carbon monoxide and hydrogen in the presence of a catalyst to produce aldehydes or alcohols as their hydrogenated products, is known as hydroformylation reaction. As the catalyst for the hydroformylation reaction, it is common to use an element of Group 8 to 10 of the Periodic Table (hereinafter referred to as a "Group VIII metal"), such as rhodium, modified by a ligand containing phosphorus. It is known that the reaction activity and the selectivity of the product are substantially changed by the ligand used together with the metal component of the catalyst. Accordingly, in order to carry out the hydroformylation reaction industrially advantageously, it is important to improve the reaction activity and the selectivity of the product, and to suppress an olefin-reduced product by a side-reaction. Accordingly, various efforts to design the ligand have been made for this purpose. As such processes, hydroformylation processes employing various phosphine compounds, and hydroformylation processes employing various phosphite compounds, have been reported.

Very few examples have been reported wherein a phosphonite compound is used as the ligand for the hydroformylation reaction. Fewer examples have been reported wherein a phosphonite compound which is not monodentate is used. For example, U.S. Pat. No. 4,400,547 discloses that in a process for a hydroformylation reaction of an olefin employing a non-modified Rh metal as a catalyst, in a step of separating the catalyst, $PhP(OPh)_2$ or $EtP(OPh)_2$ is added as an organic phosphorus compound to stabilize rhodium. However, the ligand in the phosphonite compound is removed after the step of separating the catalyst, and it is not shown that the phosphonite ligand is effective for the oxo reaction system. Further, He Binglin et al. have reported an example wherein a hydroformylation reaction of diisobutylene is carried out by using an Rh catalyst and a phosphonite compound bonded to a polymer having many functional groups introduced thereto or to a styrene-divinylbenzene copolymer (<polymer>-$P(OEt)_2$). This document describes that results of a degree of conversion of 64.3%, an yield of aldehyde of 60.8% and an yield of alcohol of 3.5%, were obtained at a reaction temperature of 110° C. under a reaction pressure of 100 atm for a reaction time of 6 hours (Sci. Cin. Ser. B(Engl. Ed.), 31(3), 269 (1988)). As mentioned above, a very few examples have been made wherein a hydroformylation reaction is carried out by using a phosphonite compound, and fewer examples have been made wherein a phosphonite compound which is not monodentate is used. Further, no example has been known, which reports that a homogeneous complex catalyst containing a bidentate phosphonite compound is effective for the hydroformylation reaction of an olefinic compound.

Further, the activity of the hydroformylation reaction employing a known phosphorus ligand such as a monodentate or bidentate phosphine or a monodentate or bidentate phosphite, has not necessarily been satisfied, and the formation of by-products has brought about an economical disadvantage to commercial production. Among such by-products, paraffins formed by reduction of an olefinic compound by hydrogen gas without a hydroformylation reaction, are particularly valueless. Accordingly, it has strongly been desired to develop a ligand which does not cause a side-reaction such as the hydrogenation reaction.

DISCLOSURE OF THE INVENTION

In the course of a search for an effective ligand to improve and maintain the reaction activity and the selectivity of the desired product in the hydroformylation reaction, the present inventors have found that by carrying out the hydroformylation reaction in the presence of a Group VIII metal compound having a phosphonite compound with a certain specific structure as a ligand, good results can be obtained with respect to the reaction activity and the selectivity of a straight chain isomer as an aldehyde product, and at the same time, the reduction reaction of the olefinic compound as a side-reaction can be suppressed. The present invention has been accomplished on the basis of these discoveries.

Namely, the present invention provides a method for producing aldehydes, which comprises reacting an olefinic compound with carbon monoxide and hydrogen, in the presence of a catalyst containing a metal of Group 8 to 10 (hereinafter referred to as "Group VIII metal") and a trivalent organic phosphorus compound to produce the corresponding aldehydes, wherein a cyclic or non-cyclic, particularly a bidentate cyclic or bidentate non-cyclic, phosphonite compound of any one of the following general formulae (I) to (V), is employed, as the trivalent organic phosphorus compound:

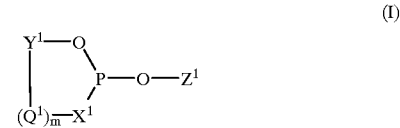

(I)

wherein $Z^1$ is a substituted or unsubstituted hydrocarbon group, each of $X^1$ and $Y^1$ is a substituted or unsubstituted bivalent hydrocarbon group, substituents in $X^1$ and $Y^1$ may further together form a bond, $Q^1$ is a substituted or unsubstituted methylene group, and m is 0 or a positive integer;

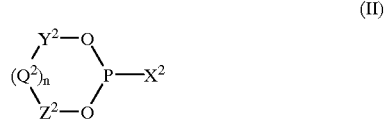

(II)

wherein $X^2$ is a substituted or unsubstituted hydrocarbon group, each of $Y^2$ and $Z^2$ is a substituted or unsubstituted bivalent hydrocarbon group, substituents in $X^2$ and $Y^2$ may further together form a bond, $Q^2$ is a substituted or unsubstituted methylene group, and n is 0 or a positive integer;

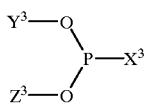

(III)

wherein X³ is a substituted or unsubstituted hydrocarbon group, and each of Y³ and Z³ is a substituted or unsubstituted aromatic hydrocarbon group;

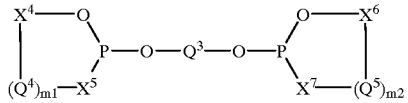

(IV)

wherein each of X⁴, X⁵, X⁶ and X⁷ is a substituted or unsubstituted bivalent hydrocarbon group, substituents in X⁴, X⁵, X⁶ and X⁷ may further together form a bond, Q³ is a substituted or unsubstituted bivalent hydrocarbon group, each of Q⁴ and Q⁵ is a substituted or unsubstituted methylene group, and each of m1 and m2 is 0 or a positive integer;

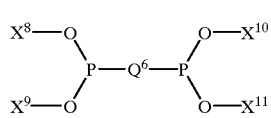

(V)

wherein each of X⁸, X⁹, X¹⁰ and X¹¹ is a substituted or unsubstituted hydrocarbon group, and Q⁶ is a bivalent organic group.

In the hydroformylation reaction employing the phosphonite compound of the present invention, a high reaction activity and a high selectivity of a straight chain isomer as an aldehyde product, can be obtained, and the reduction of the olefinic compound as a side-reaction can be suppressed. Accordingly, the hydroformylation reaction can be carried out industrially advantageously.

BEST MODE FOR CARRYING OUT THE INVENTION

Now, the present invention will be described in detail.

The cyclic phosphonite compound represented by the general formula (I) to be used in the present invention, is a phosphonite compound having a cyclic structure containing a P—O bond in its molecule.

In the general formula (I), the substituted or unsubstituted hydrocarbon group represented by Z¹ may be a C₁₋₃₀ alkyl group which may be branched, a cycloalkyl group, an alkenyl group which may be branched, or a C₆₋₃₀ aryl group. The alkyl group may, for example, be a methyl group, an ethyl group, a propyl group, a butyl group or an octyl group. The cycloalkyl group may, for example, be a cyclopropyl group, a cyclopentyl group or a cyclohexyl group. The alkenyl group may, for example, be a vinyl group, an allyl group or a 2-cyclohexenyl group. The aryl group may, for example, be a phenyl group, a 1-naphthyl group or a 2-naphthyl group.

The substituted or unsubstituted bivalent hydrocarbon group represented by each of X¹ and Y¹, may, for example, be a C₁₋₃₀ alkylene group, cycloalkylene group, alkenylene group or an arylene group or a C₆₋₃₀ arylene group. Specifically, it may, for example, be a methylene group, an ethylene group, a 1,2-phenylene group or a naphthylene group. The substituent for each of X¹, Y¹ and Z¹, may, for example, be a C₁₋₃₀, preferably C₁₋₈, alkyl group, a cycloalkyl group, a C₆₋₂₂, preferably C₆₋₁₄, aryl group, a C₁₋₃₀, preferably C₁₋₈, alkoxy group, a C₇₋₃₀ alkyl aryl group, an aryl alkyl group, an acyl group, a carbonyloxy group, an oxycarbonyl group, a sulfonyl group, a sulfinyl group, a silyl group, an alkylamino group, a hydroxyl group, an amino group, a cyano group, a nitro group or a halogen atom. From 1 to 3 such substitutents may be substituted on each of hydrocarbon groups of X¹, Y¹ and Z¹, and the substituents may be the same or different. Q¹ is a substituted or unsubstituted methylene group, and m is 0 or positive integer, and preferably m=0.

Among the phosphonite compounds represented by the general formula (I), a compound represented by the following general formula (I') wherein X¹ and Y¹ are aromatic hydrocarbon groups, is preferred:

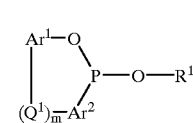

(I')

wherein R¹ is a substituted or unsubstituted hydrocarbon group, each of Ar¹ and Ar² is a substituted or unsubstituted bivalent aromatic hydrocarbon group, substituents in Ar¹ and Ar² may further together form a bond, Q¹ is a substituted or unsubstituted methylene group, and m is 0 or a positive integer.

In the above mentioned general formula (I'), the hydrocarbon group represented by R¹ may be a C₁₋₃₀ alkyl group, a cycloalkyl group, an aryl group, an alkyl aryl group or an aryl alkyl group, and the aromatic hydrocarbon group represented by each of Ar¹ and Ar², may, for example, be a substituted or unsubstituted C₆₋₃₀ bivalent arylene group such as a phenylene group or a naphthylene group.

Specifically, R¹ may, for example, be a phenyl group, a 2-methylphenyl group, a 2-ethylphenyl group, a 2-t-butylphenyl group, a 2,4-di-t-butylphenyl group, a 2,4-di-t-butyl-6-phenylphenyl group, a 2,4-di-t-butyl-6-nitrophenyl group, a 2,4-di-t-butyl-6-methylphenyl group, a 2-t-butyl-4-methoxyphenyl group, a 2-t-butyl-4-methylphenyl group, a 2-t-butyl-6-methylphenyl group, a 2,4-dimethylphenyl group, a 2,6-di-t-butyl-4-methoxyphenyl group, a 2,6-di-t-butyl-4-methoxycarbonylphenyl group, a 4-nitrophenyl group, a 4-cyanophenyl group, a 4-dimethylaminophenyl group, a 1-naphthyl group, a 2-naphthyl group, a 3,6-di-t-butyl-2-naphthyl group, a butyl group, a phenylmethyl group or a 2-phenylethyl group. Among these, a phenyl group, a 2,4-di-t-butylphenyl group, a 2,4-di-t-butyl-6-phenylphenyl group and a 3,6-di-t-butyl-2-naphthyl group are preferred.

Further, preferably m is 0 or 1, more preferably m=0. Specifically, the bivalent group Ar¹—(Q¹)ₘ—Ar² may, for example, be a 2,2'-biphenyldiyl group, a 3,5-di-t-butyl-2,2'-biphenyldiyl group, a 5,5'-dimethyl-2,2'-biphenyldiyl group, a 3-phenyl-2,2'-biphenyldiyl group, a 3,5-diphenyl-2,2'-biphenyldiyl group, a 3-cyclohexyl-2,2'-biphenyldiyl group, a 4,4'-dimethyl-2,2'-biphenyldiyl group, a 4,4'-t-butyl-2,2'-biphenyldiyl group, a 3-methyl-2,2'-biphenyldiyl group, a 5-methyl-2,2'-biphenyldiyl group, a 5-(2-phenylethyl)-2,2'- biphenyldiyl group, a 5-methoxy-2,2'-biphenyldiyl group, a 4-methyl-2,2'-biphenyldiyl group, a 4-t-butyl-2,2'-biphenyldiyl group, a 1,1'-bi-2-naphthyl group, a 3-methyl-1,1'-bi-2-naphthyl group, a 3-t-butyl-1,1'-bi-2-naphthyl group or a 3,6,3',6'-tetra-t-butyl-1,1'-bi-2-naphthyl group (here, the number without "'" means a substituted position on $Ar^1$, and the number with "'" means a substituted position on $Ar^2$). Among these, 2,2'-biphenyldiyl group and a 3,5-di-t-butyl-2,2'-biphenyldiyl group are preferred.

The substituent for each of $R^1$, $Ar^1$ and $Ar^2$, is as mentioned for the substituent for each of $X^2$, $Y^2$ and $Z^2$ in the above mentioned general formula (I).

Representative examples of the phosphonite compound of the present invention represented by the general formula (I') will be given below.

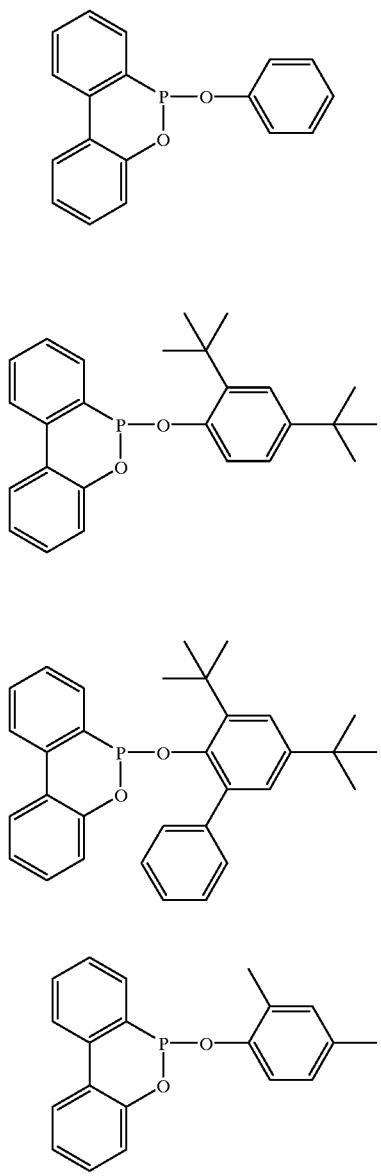

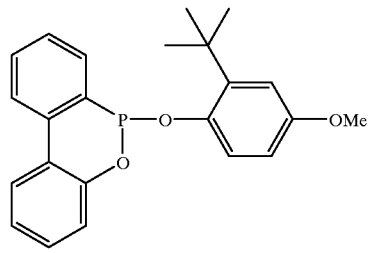

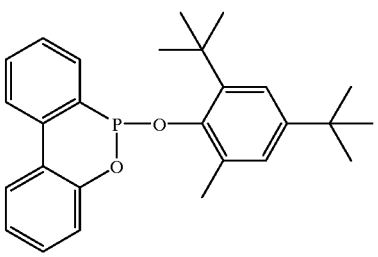

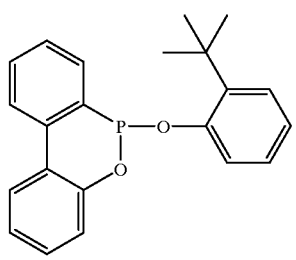

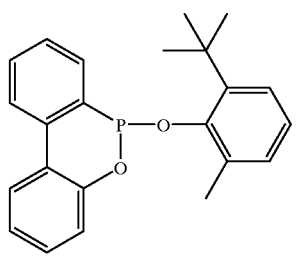

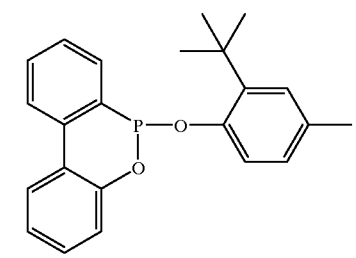

(11)
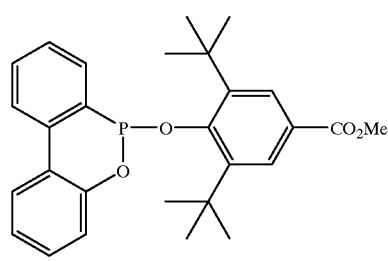
(12)
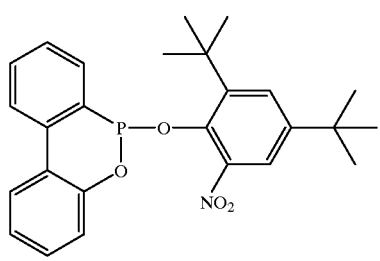
(13)
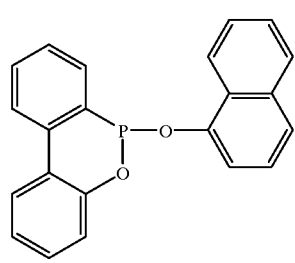
(14)
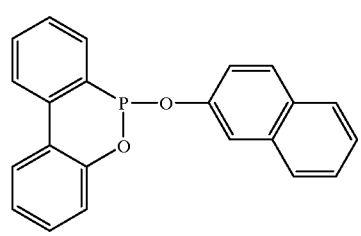
(15)
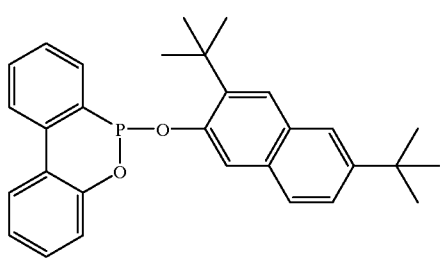
(16)
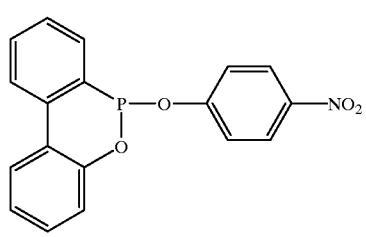
(17)
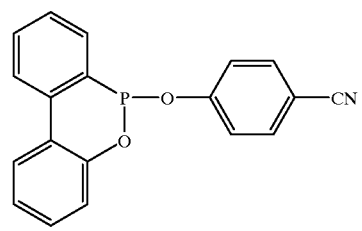
(18)
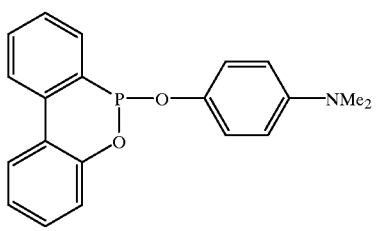
(19)
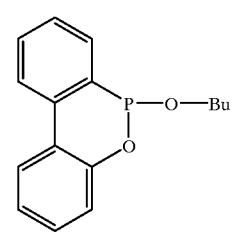
(20)
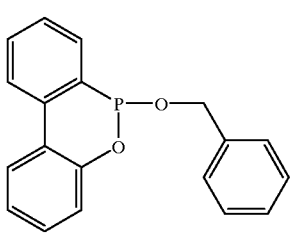
(21)
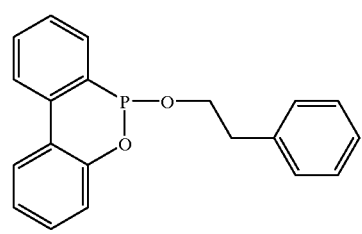
(22)
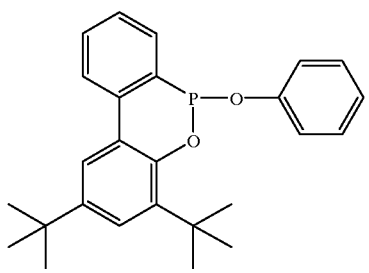

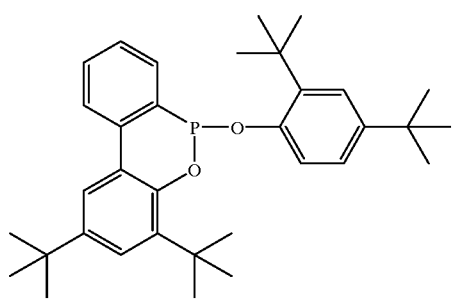
(23)
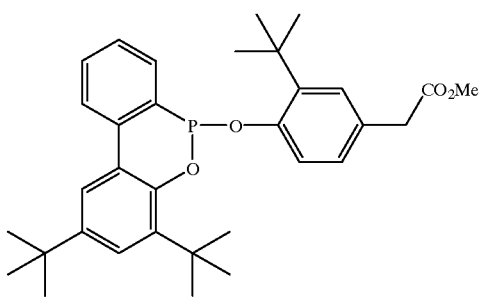
(28)
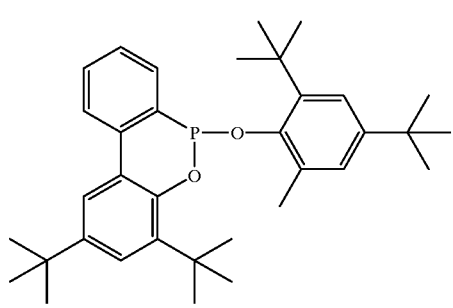
(24)
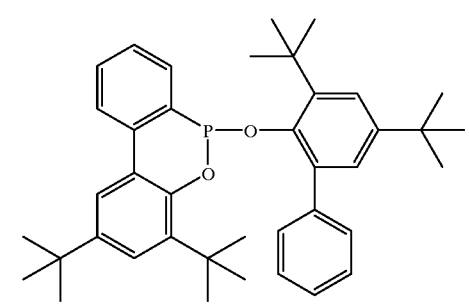
(29)
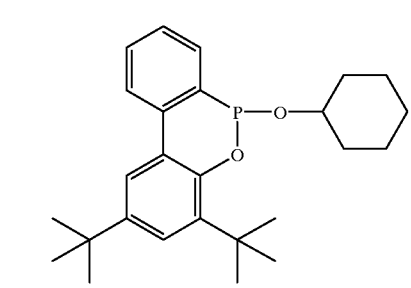
(25)
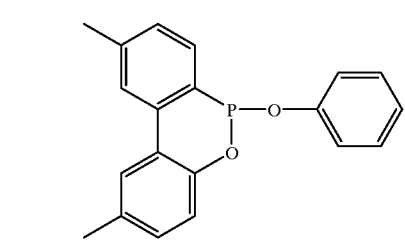
(30)
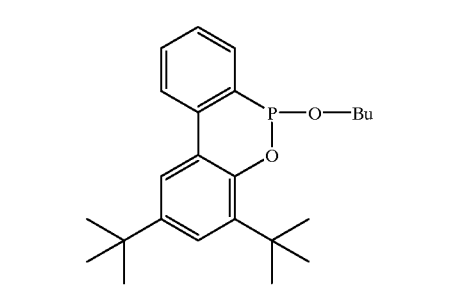
(26)
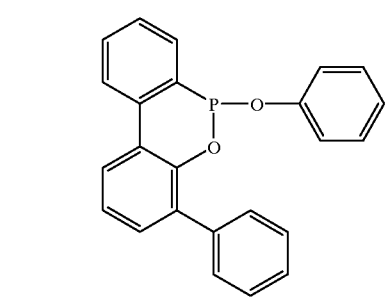
(31)
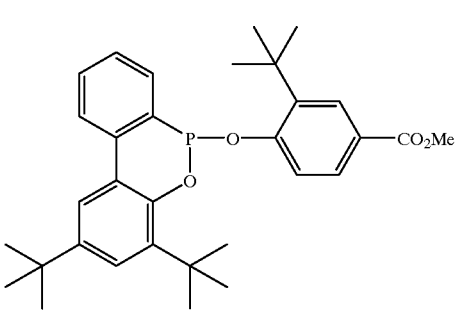
(27)
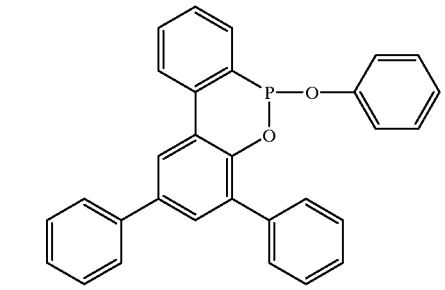
(32)

-continued

(33)
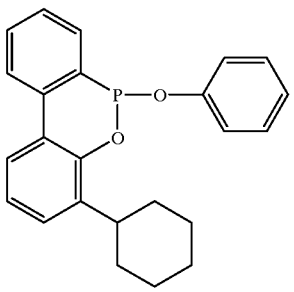

(34)
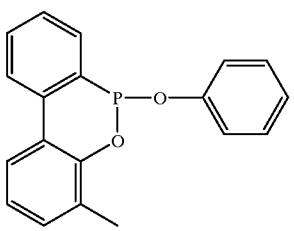

(35)
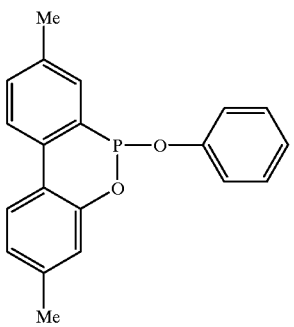

(36)
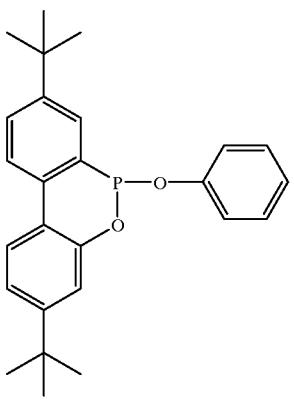

The phosphonite compound represented by the general formula (I') can be prepared, for example, by the following synthesis method. For example, substituted or unsubstituted o-phenylphenol is reacted with phosphorus trichloride in the presence of zinc chloride, and a 6-chloro-6H-dibenzo[c,e][1,2]oxaphosphorin derivative can be produced with a high yield. Then, an alcohol or a phenol compound, represented by $R^1$—OH using the symbol in the general formula (I'), is reacted therewith in the presence of a base such as an amine or pyridine, and the corresponding phosphonite compound can easily be produced. In this case, a solvent may be used, and as the solvent, e.g. toluene, hexane, tetrahydrofuran (THF) or diethylether may be used.

Further, as the phosphonite compound to be used in the present invention, a phosphonite compound represented by the following general formula (II) may be mentioned:

(II)
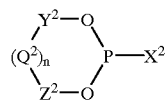

wherein $X^2$ is a substituted or unsubstituted hydrocarbon group, each of $Y^2$ and $Z^2$ is a substituted or unsubstituted bivalent hydrocarbon group, substituents in $Y^2$ and $Z^2$ may further together form a bond, $Q^2$ is a substituted or unsubstituted methylene group, and n is 0 or a positive integer.

In the general formula (II), the substituted or unsubstituted hydrocarbon group represented by $X^2$, may be a $C_{1-30}$ alkyl group which may be branched, a cycloalkyl group, an alkenyl group which may be branched, or a $C_{6-30}$ aryl group. The alkyl group may, for example, be a methyl group, an ethyl group, a propyl group, a butyl group or an octyl group. The cycloalkyl group may, for example, be a cyclopropyl group, a cyclopentyl group or a cyclohexyl group. The alkenyl group may, for example, be a vinyl group, an allyl group or a 2-cyclohexenyl group. The aryl group may, for example, be a phenyl group, a 1-naphthyl group or a 2-naphthyl group.

The substituted or unsubstituted bivalent hydrocarbon group represented by each of $Y^2$ and $Z^2$, may, for example, be a $C_{1-30}$ alkylene group, a cycloalkylene group, an alkenylene group, an arylene group or a $C_{6-30}$ arylene group. Specifically, it may, for example, be a methylene group, an ethylene group, a 1,2-phenylene group or a naphthylene group. The substituent for each of $X^2$, $Y^2$ and $Z^2$ may, for example, be a $C_{1-30}$, preferably $C_{1-8}$, alkyl group, a cycloalkyl group, a $C_{6-22}$, preferably $C_{6-14}$ aryl group, a $C_{1-30}$, preferably $C_{1-8}$, alkoxy group, a $C_{7-30}$ alkyl aryl group, an aryl alkyl group, an acyl group, a carbonyloxy group, an oxycarbonyl group, a sulfonyl group, a sulfinyl group, a silyl group, an alkyl amino group, a hydroxyl group, an amino group, a cyano group, a nitro group or a halogen atom. From 1 to 3 such substituents may be substituted on each of hydrocarbon groups of $Y^2$ and $Z^2$, and the substituents may be the same or different. $Q^2$ is a substituted or unsubstituted methylene group, and n is preferably 0 or 1.

Among the phosphonite compounds represented by the general formula (II), a compound represented by the following general formula (II') wherein $Y^2$ and $Z^2$ are aromatic hydrocarbon groups, is preferred:

(II')
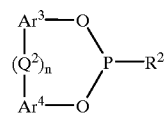

wherein $R^2$ is a substituted or unsubstituted hydrocarbon group, each of $Ar^3$ and $Ar^4$ is a substituted or unsubstituted bivalent aromatic hydrocarbon group, substituents in $Ar^3$ and $Ar^4$ may further together form a bond, $Q^2$ is a substituted or unsubstituted methylene group, and n is 0 or a positive integer.

In the above formula (II'), the substituted or unsubstituted hydrocarbon group represented by $R^2$, may be a $C_{1-30}$ alkyl group, a cycloalkyl group, an aryl group, an alkyl aryl group or an aryl alkyl group, and the aromatic hydrocarbon group represented by each of $Ar^3$ and $Ar^4$ may, for example, be a substituted or unsubstituted $C_{6-30}$ bivalent arylene group such as a phenylene group or a naphthylene group.

Specifically, $R^2$ may, for example, be a phenyl group, a 2-methylphenyl group, a 2-ethylphenyl group, a 2-t-butylphenyl group, a 2,4-dimethylphenyl group, a 2,4-di-t-butylphenyl group, a 2-t-butyl-6-methylphenyl group, a 2-t-butyl-4-methoxyphenyl group, a 2-t-butyl-4-methylphenyl group, a 2,4-di-t-butyl-6-phenylphenyl group, a 2,4-di-t-butyl-6-nitrophenyl group, a 2,4-di-t-butyl-6-methylphenyl group, a 2,6-di-t-butyl-4-methoxyphenyl group, a 2,6-di-t-butyl-4-methoxycarbonylphenyl group, a 4-nitrophenyl group, a 4-cyanophenyl group, a 4-dimethylaminophenyl group, a 1-naphthyl group, a 2-naphthyl group, a 3,6-di-t-butyl-2-naphthyl group, a butyl group, a phenylmethyl group or a 2-phenylethyl group. Among these, a phenyl group, a 2-methylphenyl group, a 2-ethylphenyl group, a 1-naphthyl group and a 2-naphthyl group are preferred.

Further, in the general formula (II'), $Q^2$ is a substituted or unsubstituted methylene group, and n is preferably 0 or 1. Specifically, the bivalent group $Ar^3-(Q^2)_n-Ar^4$ may, for example, be a 2,2'-biphenyldiyl group, a 3,3'-dimethyl-2,2'-biphenyldiyl group, a 3,3'-di-t-butyl-2,2'-biphenyldiyl group, a 3,3'-di-t-butyl-5,5'-dimethyl-2,2'-biphenyldiyl group, a 3,3'-di-t-butyl-5,5'-diethyl-2,2'-biphenyldiyl group, a 3,3'-dimethoxy-5,5'-dimethyl-2,2'-biphenyldiyl group, a 3,5,3',5'-tetra-t-butyl-2,2'-biphenyldiyl group, a 3,5,3',5'-tetramethyl-2,2'-biphenyldiyl group, a 1,1'-bi-2-naphthyl group, a 3,3'-dimethyl-1,1'-bi-2-naphthyl group, a 3,3'-di-t-butyl-1,1'-bi-2-naphthyl group, a methylenebis(2-phenyl) group, a methylenebis(5-methyl-2-phenyl) group, a methylenebis(5-chloro-2-phenyl) group, a methylenebis(3,5,6-trichloro-2-phenyl) group, a methylenebis(3-t-butyl-5-methyl-2-phenyl) group, a methylenebis(3,5-di-t-butyl-2-phenyl) group, an α-methylmethylenebis(3,5-di-t-butyl-2-phenyl) group, a methylenebis(3,5-dibromo-2-phenyl) group, a methylenebis(3-cyclohexyl-5-methyl-2-phenyl) group or a methylenebis(1,1'-bi-2-naphthyl) group. Among these, a 2,2'-biphenyldiyl group, a 3,5,3',5'-tetra-t-butyl-1,1'-bi-2-naphthyl group, a 3,5,3',5'-tetra-t-butyl-2,2'-bi-1-naphthyl group, a methylenebis(2-phenyl) group and a methylenebis(3-t-butyl-5-methyl-2-phenyl) group are preferred. Further, the substituent for each of $R^2$, $Ar^3$ and $Ar^4$, is as mentioned for the substituent for each of $X^2$, $Y^2$ and $Z^2$ in the above mentioned general formula (II).

Representative examples of the phosphonite compound of the present invention represented by the general formula (II') will be given below.

(37)

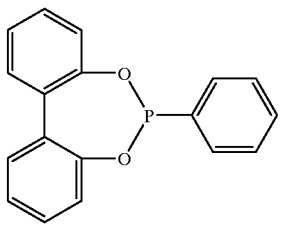

(38)

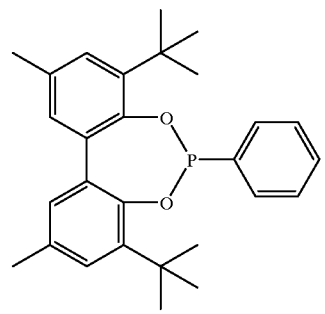

(39)

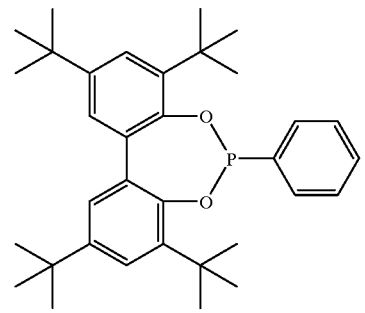

(40)

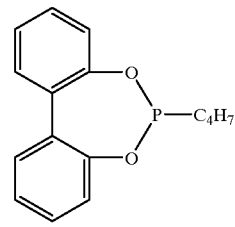

(41)

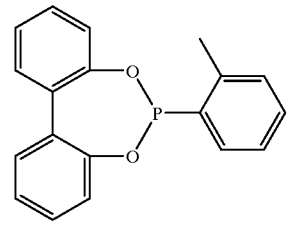

(42)

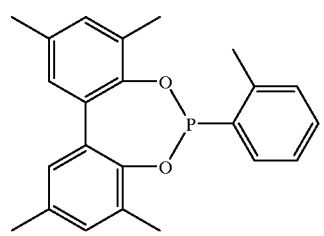

(43)
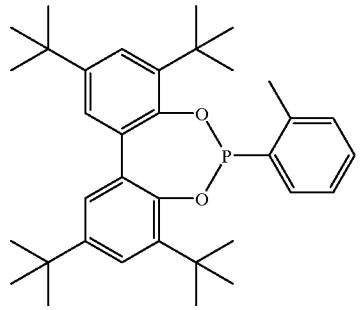
(44)
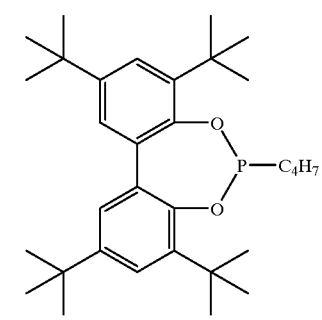
(45)
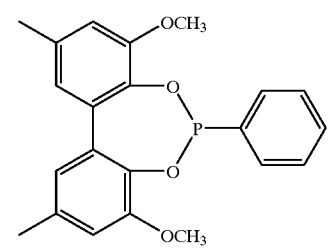
(46)
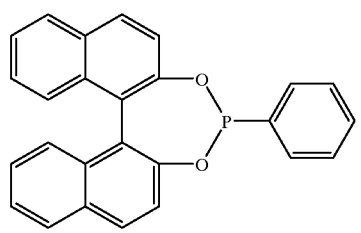
(47)
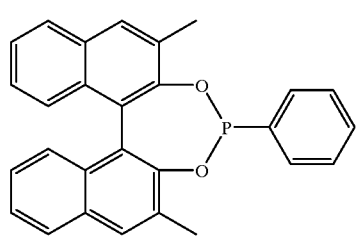
(48)
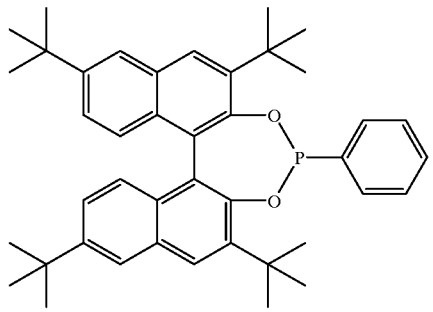
(49)
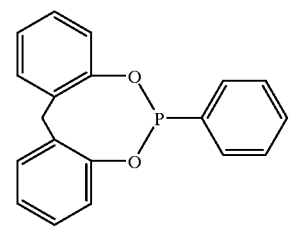
(50)
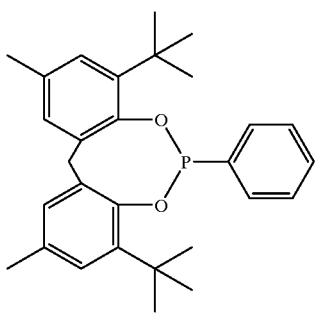
(51)
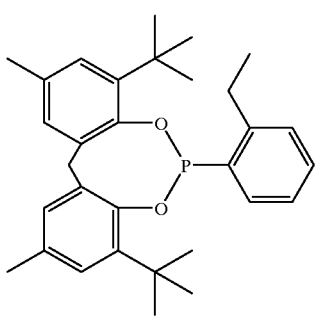
(52)
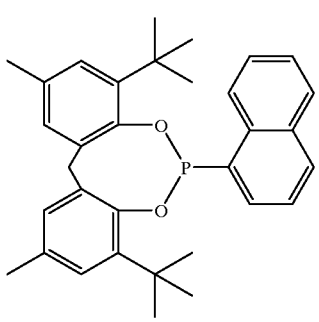

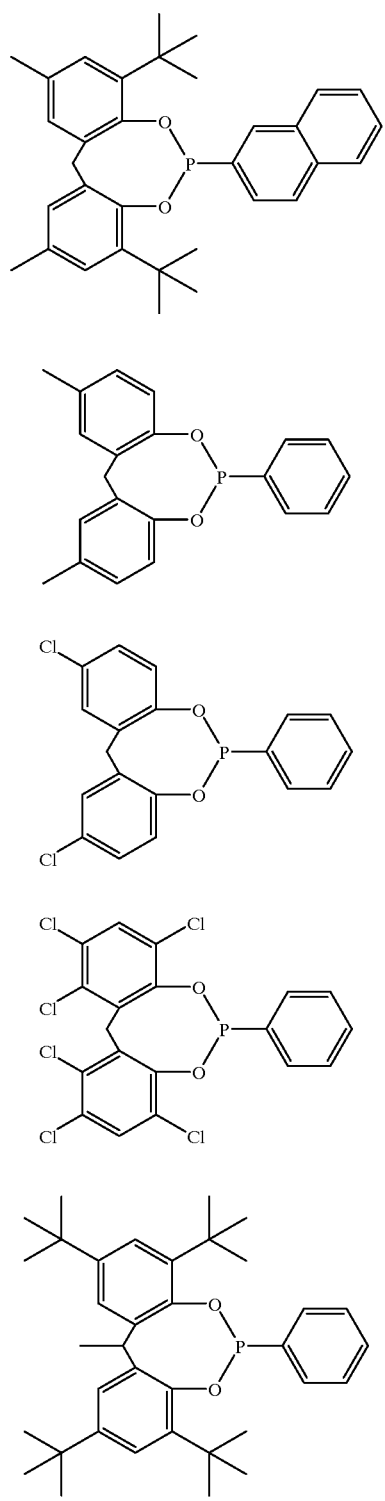

(53)
(54)
(55)
(56)
(57)

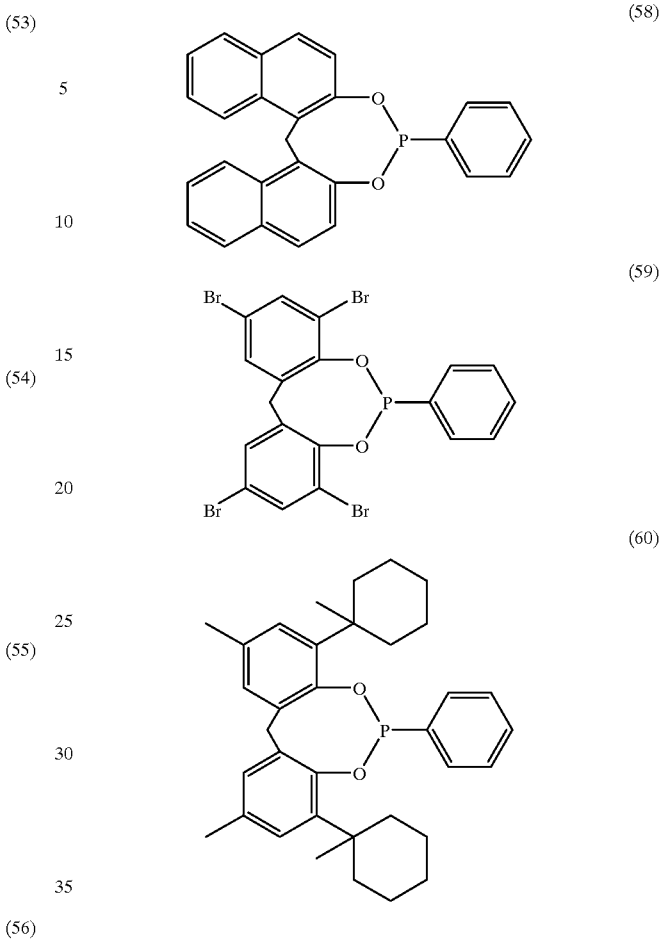

(58)
(59)
(60)

In the non-cyclic phosphonite compound represented by the general formula (III) to be used in the present invention, each of $X^3$, $Y^3$ and $Z^3$ is a substituted or unsubstituted hydrocarbon group, and no bonding is formed among these. The hydrocarbon group may be a $C_{1-30}$ alkyl group which may be branched, a cycloalkyl group, an alkenyl group which may be branched, or a $C_{6-30}$ aryl group. The alkyl group may, for example, be a methyl group, an ethyl group, a propyl group, a butyl group or an octyl group. The cycloalkyl group may, for example, be a cyclopropyl group, a cyclopentyl group or a cyclohexyl group. The alkenyl group may, for example, be a vinyl group, an allyl group or a 2-cyclohexenyl group. The aryl group may, for example, be a phenyl group, a 1-naphthyl group or a 2-naphthyl group.

The substituent for each of the hydrocarbon groups $X^3$, $Y^3$ and $Z^3$ may, for example, be a $C_{1-30}$, preferably $C_{1-8}$, alkyl group, a cycloalkyl group, a $C_{6-22}$, preferably $C_{6-14}$, aryl group, a $C_{1-30}$, preferably $C_{1-8}$, alkoxy group, a $C_{7-30}$ alkyl aryl group, an aryl alkyl group, an acyl group, a carbonyloxy group, an oxycarbonyl group, a sulfonyl group, a sulfinyl group, a silyl group, an alkylamino group, a hydroxyl group, an amino group, a cyano group, a nitro group or a halogen atom. The alkyl group as the substituent, may, for example, be a methyl group, an ethyl group, a propyl group, a butyl group or an octyl group. The cycloalkyl group may, for example, be a cyclopropyl group, a cyclopentyl group or a cyclohexyl group. The alkenyl group may, for example, be a vinyl group, an allyl group or a 2-cyclohexenyl group. The aryl group may, for example, be a phenyl group, a 1-naphthyl group or a 2-naphthyl group. From 1 to 3 such substituents may be substituted on each of hydrocarbon groups of $X^3$, $Y^3$ and $Z^3$, and the substituents may be the same or different.

Among the compounds represented by the general formula (III), a non-cyclic phosphonite compound represented by the following general formula (II) wherein $Y^3$ and $Z^3$ are aromatic hydrocarbon groups, is preferred:

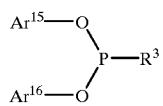

(III')

wherein $R^3$ is a substituted or unsubstituted hydrocarbon group, and each of $Ar^{15}$ and $Ar^{16}$ is a substituted or unsubstituted aromatic hydrocarbon group.

In the general formula (III'), $R^3$ is as defined for $X^3$ in the general formula (III), and the aromatic hydrocarbon group represented by each of $Ar^{15}$ and $Ar^{16}$ is a substituted or unsubstituted $C_{6-30}$ aryl group.

Specifically, $R^3$ may, for example, be a methyl group, an ethyl group, a butyl group, a hexyl group, an octyl group, a cyclohexyl group, a cyclooctyl group, a phenyl group, a 2-ethylphenyl group, a 2-i-propylphenyl group, a 2-t-butylphenyl group, a 1-naphthyl group or a 2-naphthyl group. Among these, a phenyl group and a 2-i-propylphenyl group are preferred.

Specifically, each of $Ar^{15}$ and $Ar^{16}$ may, for example, be a phenyl group, a 2,4-di-t-butylphenyl group, a 2-t-butyl-4-methoxyphenyl group, a 2-cyclohexyl-4-methylphenyl group, a 4-cyano-2-methoxyphenyl group, a 2,4-dichlorophenyl group, a 1-naphthyl group, a 9-phenanthryl group or a 3,6-di-t-butyl-2-naphthyl group. Among these, as each of $Ar^{15}$ and $Ar^{16}$, a phenyl group, a 2,4-di-t-butylphenyl group and a 3,6-di-t-butyl-2-naphthyl group are preferred. Here, it is preferred that at least one of $Ar^{15}$ and $Ar^{16}$ is an aromatic hydrocarbon group having a substituent.

The substituent for each of $R^3$, $Ar^{15}$ and $Ar^{16}$ may, for example, be a $C_{1-30}$, preferably $C_{1-8}$, alkyl group, a cycloalkyl group, a $C_{6-22}$, preferably $C_{6-14}$, aryl group, a $C_{1-30}$, preferably $C_{1-8}$, alkoxy group, a $C_{7-30}$ alkyl aryl group, an aryl alkyl group, an acyl group, a carbonyloxy group, an oxycarbonyl group, a sulfonyl group, a sulfinyl group, a silyl group, an alkylamino group, a hydroxyl group, an amino group, a cyano group, a nitro group or a halogen atom. From 1 to 3 such substituents may be substituted on each of the hydrocarbon groups of $R^3$, $Ar^{15}$ and $Ar^{16}$, and the substituents may be the same or different.

Representative examples of the non-cyclic phosphonite compound represented by the general formula (III') will be given below.

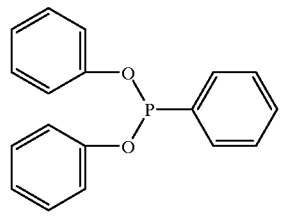
(61)

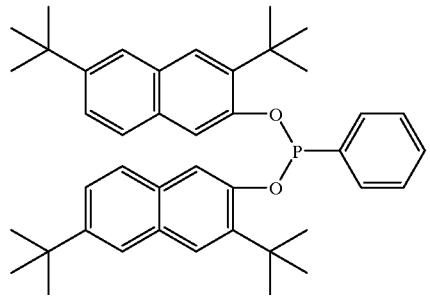
(62)

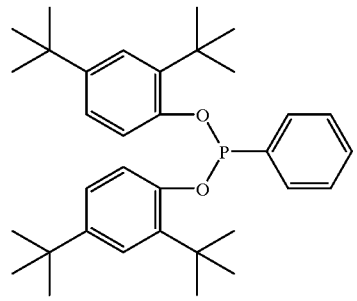
(63)

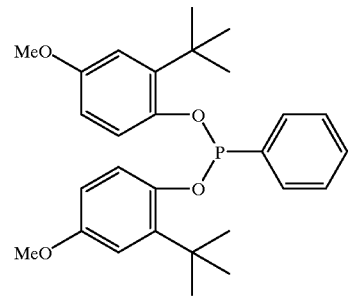
(64)

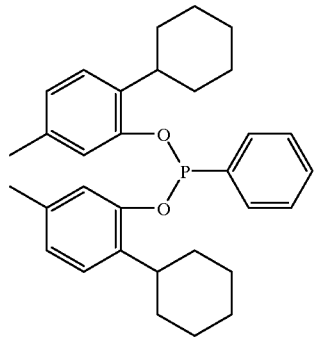
(65)

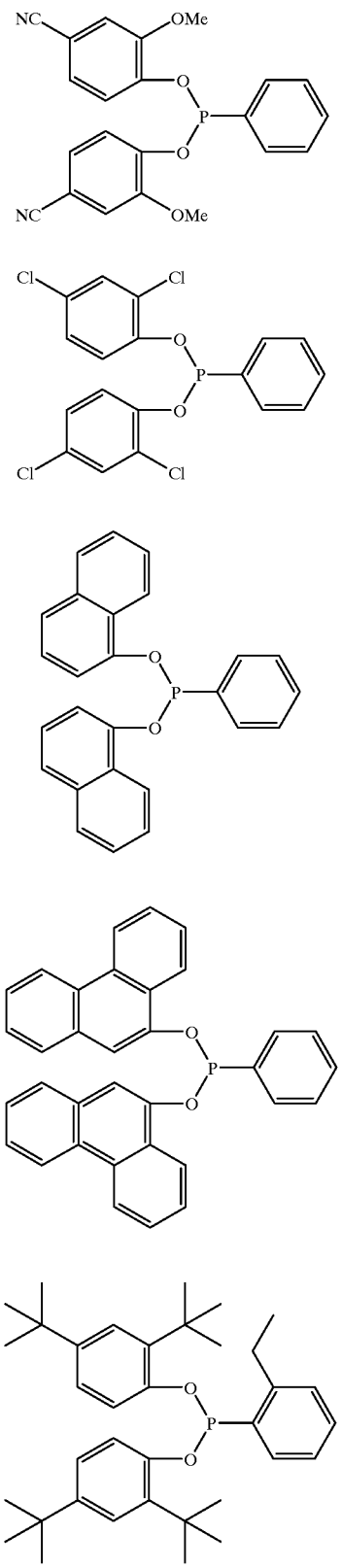

(66)
(67)
(68)
(69)
(70)

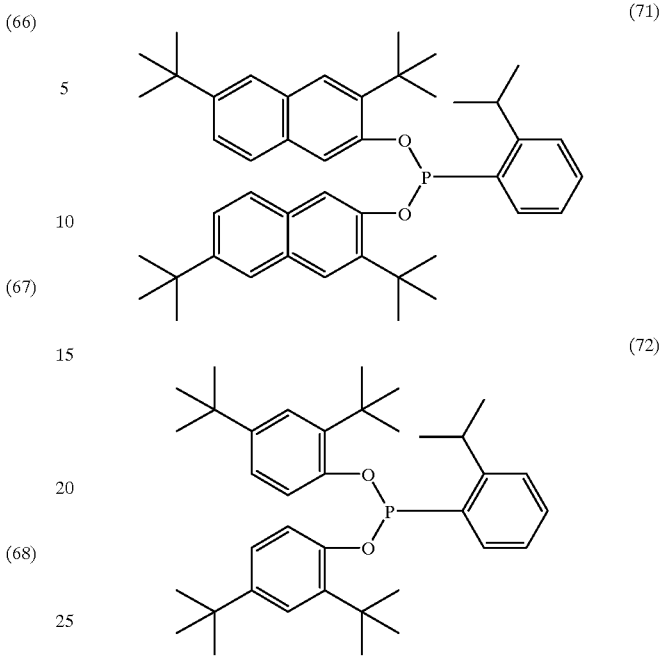

(71)
(72)

The bidentate cyclic phosphonite compound represented by the general formula (IV) to be used in the present invention, is a bidentate phosphonite compound having a cyclic structure containing a C—P—O bond in its molecule.

In the general formula (VI), the substituted or unsubstituted bivalent hydrocarbon group represented by $Q^3$, may, for example, be a $C_{1-30}$ alkylene group, a cycloalkylene group, an alkenylene group, a $C_{6-30}$ arylene group, and an organic group comprising the plurality of them.

The substituted or unsubstituted bivalent hydrocarbon group represented by each of $X^4$, $X^5$, $X^6$ and $X^7$, may, for example, be a $C_{1-30}$ alkylene group, a cycloalkylene group, an alkenylene group or a $C_{6-30}$ arylene group. Specifically, it may, for example, be a methylene group, an ethylene group, a 1,2-phenylene group, 1,2-naphthylene group or a 2,3-naphthylene group. The substituent for each of $X^4$, $X^5$, $X^6$, $X^7$, $Q^3$, $Q^4$ and $Q^5$, may, for example, be a $C_{1-30}$, preferably $C_{1-8}$, alkyl group, a cycloalkyl group, a $C_{6-22}$, preferably $C_{6-14}$, aryl group, a $C_{1-30}$, preferably $C_{1-8}$, alkoxy group, a $C_{7-30}$ alkyl aryl group, an aryl alkyl group, an acyl group, a carbonyloxy group, an oxycarbonyl group, a sulfonyl group, a sulfinyl group, a silyl group, an alkylamino group, a hydroxyl group, an amino group, a cyano group, a nitro group or a halogen atom. From 1 to 4 such substituents may be substituted on each of hydrocarbon groups of $X^4$, $X^5$, $X^6$ and $X^7$, and the substituents may be the same or different. Each of $Q^4$ and $Q^5$ is a substituted or unsubstituted methylene group, each of m1 and m2 is 0 or a positive integer, and preferably both m1 and m2 are 0.

Among the phosphonite compounds represented by the general formula (IV), a compound represented by the following general formula (IV') wherein $X^4$, $X^5$, $X^6$ and $X^7$ are aromatic hydrocarbon groups, is preferred:

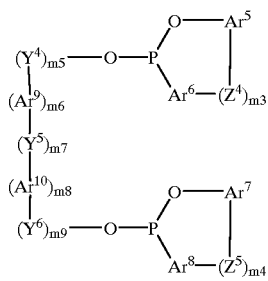

(IV')

wherein each of $Ar^5$, $Ar^6$, $Ar^7$, $Ar^8$, $Ar^9$ and $Ar^{10}$ is a substituted or unsubstituted bivalent aromatic hydrocarbon group, each of $Y^4$, $Y^5$ and $Y^6$ is a substituted or unsubstituted bivalent hydrocarbon group, substituents in $Ar^9$, $Ar^{10}$, $Y^4$, $Y^5$ and $Y^6$ may further together form a bond, each of $Z^4$ and $Z^5$ is a substituted or unsubstituted methylene group, and each of m3, m4, m5, m6, m7, m8 and m9 is 0 or a positive integer.

In the above mentioned general formula (IV'), the hydrocarbon group represented by each of $Y^4$, $Y^5$ and $Y^6$ may be a $C_{1-30}$ alkylene group, a cycloalkylene group or an arylene group, and the aromatic hydrocarbon group represented by each of $Ar^5$, $Ar^6$, $Ar^7$, $Ar^8$, $Ar^9$ and $Ar^{10}$ may, for example, be a substituted or unsubstituted $C_{6-30}$ bivalent arylene group such as a 1,2-phenylene group, a 1,2-naphthylene group or a 2,3-naphthylene group.

Further, the substituent for each of $Ar^5$, $Ar^6$, $Ar^7$, $Ar^8$, $Ar^9$, $Ar^{10}$, $Y^4$, $Y^5$, $Y^6$, $Z^4$ and $Z^5$, is as defined for the substituent for each of $X^4$, $X^5$, $X^6$, $X^7$, $Q^3$, $Q^4$ and $Q^5$ in the above mentioned general formula (IV).

In the compound represented by the general formula (IV'), each of m3, m4, m5, m6, m7, m8 and m9 is preferably 0 or 1. Specifically, the bivalent group $(Y^4)m5$-$(Ar^9)m6$-$(Y^5)m7$-$(Ar^{10})m8$-$(Y^6)m9$ may, for example, be a methylene group, an ethylene group, a 1,3-propylene group, a 1,4-butylene group, a 1,5-pentylene group, a 1,2-phenylene group, a 1,3-phenylene group, a 1,4-phenylene group, a 1,2-naphthylene group, a 2,3-naphthylene group, a 2,2'-biphenylene group, a 4,5-anthrylene group, a 4,5-phenanthrylene group, a 3,3-dimethyl-2,2'-biphenylene group, a 3,3',5,5'-tetra-t-butyl-2,2'-biphenylene group, a 2,2'-(1,1'-binaphthylene) group, a 1,1'-(2,2'-binaphthylene) group, a 3,3',6,6'-tetra-t-butyl-2,2'-(1,1'-binaphthylene) group, a 3,3'-dimethyl-2,2'-(1,1'-binaphthylene) group, a 1,2-dimethylenebenzene group, a 1,3-dimethylenebenzene group, a 1,4-dimethylenebenzene group, a 1,2-dimethylenenaphthalene group, a 2,3-dimethylenenaphthalene group, a 2,2'-dimethylenebiphenyl group, a 3,3',5,5'-tetra-t-butyl-2,2'-dimethylenebiphenyl group, a 3,3'-di-t-butyl-5,5'-dimethoxy-2,2'-dimethylenebiphenyl group, a 2,2'-dimethylene-(1,1'-binaphthalene) group, a 2,2'-dimethylene-3,3',6,6'-tetra-t-butyl-(1,1'-binaphthalene) group, a 4,5-dimethylene phenanthrene group, a 2-methylenephenyl group or a 2-t-butyl-6-methylenephenyl group.

Further, preferably m3 and m4 are 0 or 1, and more preferably both m3 and m4 are 0. Specifically, each of the bivalent groups $Ar^5$—$(Z^4)m3$-$Ar^6$ and $Ar^7$—$(Z^5)m4$-$Ar^8$, may, for example, be a 2,2'-biphenylene group, a 3,5-di-t-butyl-2,2'-biphenylene group, a 5,5'-dimethyl-2,2'-biphenylene group, a 3-phenyl-2,2'-biphenylene group, a 3,5-diphenyl-2,2'-biphenylene group, a 3-cyclohexyl-2,2'-biphenylene group, a 4,4'-dimethyl-2,2'-biphenylene group, a 4,4'-t-butyl-2,2'-biphenylene group, a 3-methyl-2,2'-biphenylene group, a 5-methyl-2,2'-biphenylene group, a 5-(2-phenylethyl)-2,2'-biphenylene group, a 5-methoxy-2,2'-biphenylene group, a 4-methyl-2,2'-biphenylene group, a 4-t-butyl-2,2'-biphenylene group, a 2,2'-(1,1'-binaphthylene) group, a 3-methyl-2,2'-(1,1'-binaphthylene) group, a 3-t-butyl-2,2'-(1,1'-binaphthylene) group, a 3,6,3',6'-tetra-t-butyl-2,2'-(1,1'-binaphthylene) group (here, the number without "'" means the substituted position in each of $Ar^5$ and $Ar^7$, and the number with "'" means the substituted position in each of $Ar^6$ and $Ar^8$). Among these, a 2,2'-biphenylene group and a 3,5-di-t-butyl-2,2'-biphenylene group are preferred.

Representative examples of the bidentate cyclic phosphonite compound represented by the general formula (IV') will be given below.

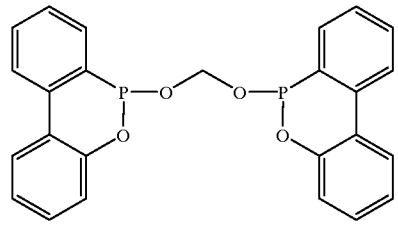

(73)

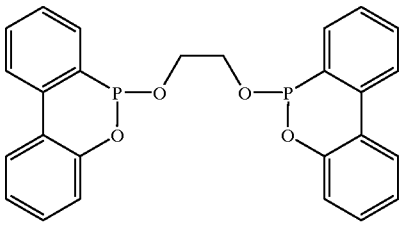

(74)

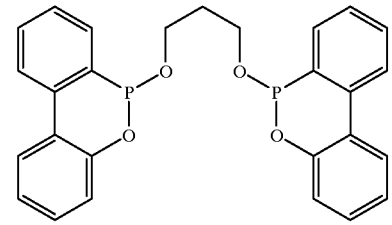

(75)

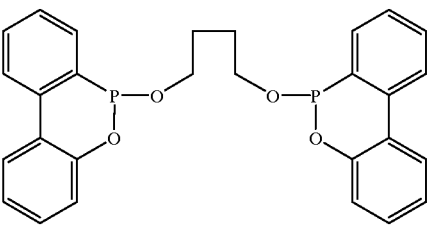

(76)

(77)
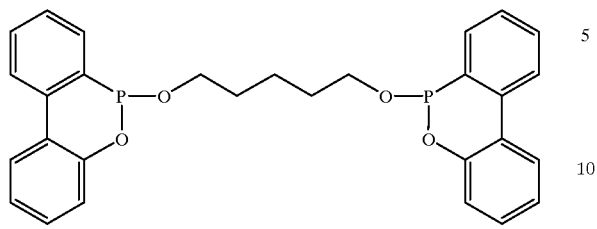
(78)
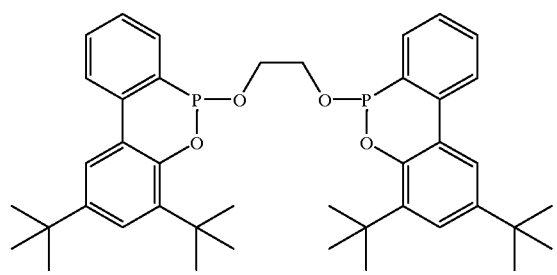
(79)
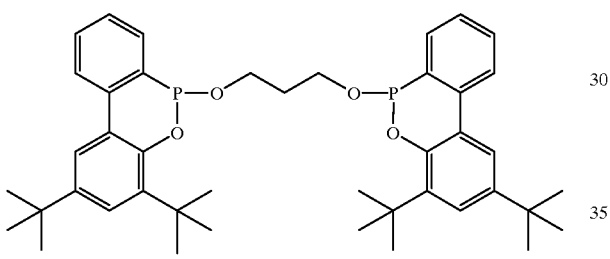
(80)
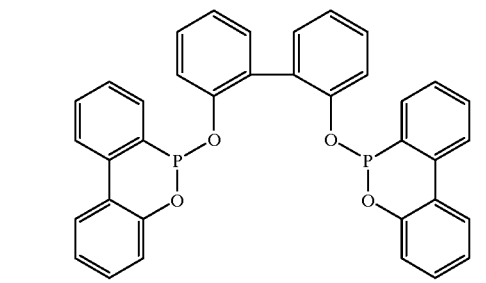
(81)
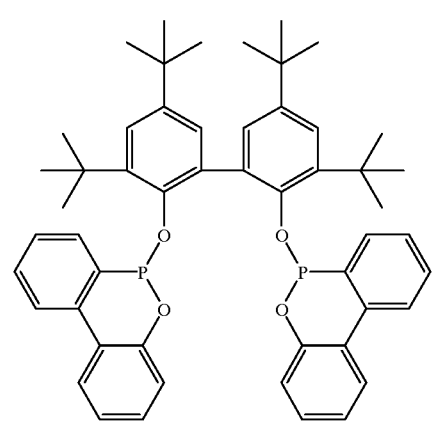
(82)
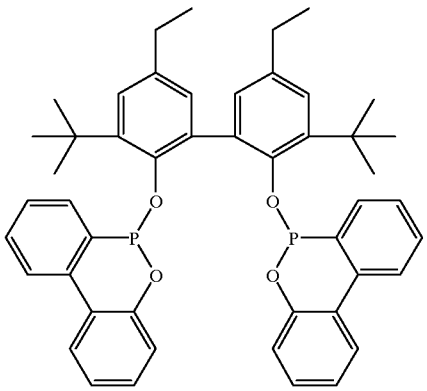
(83)
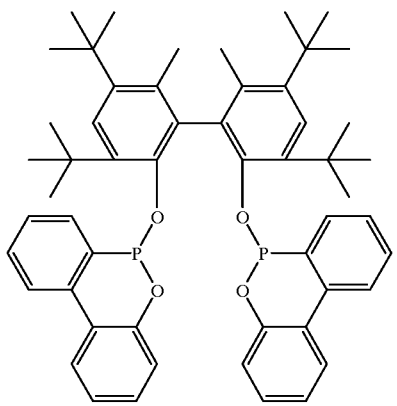
(84)
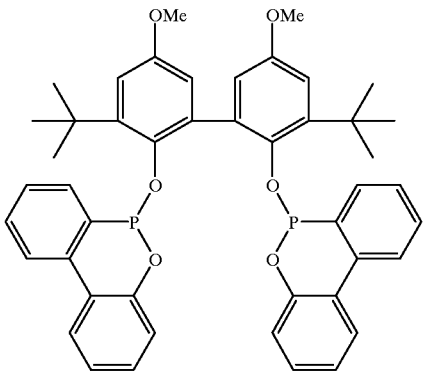
(85)
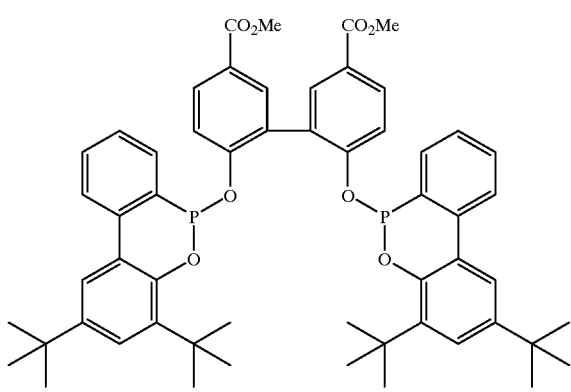

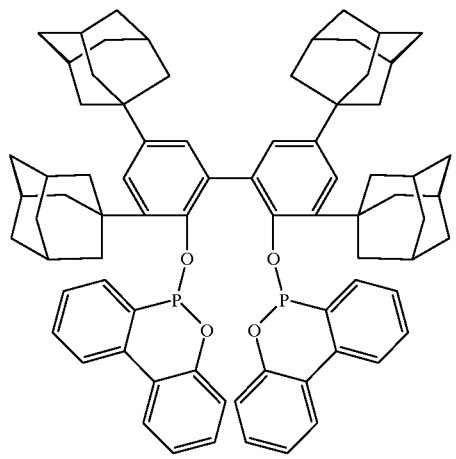
(86)
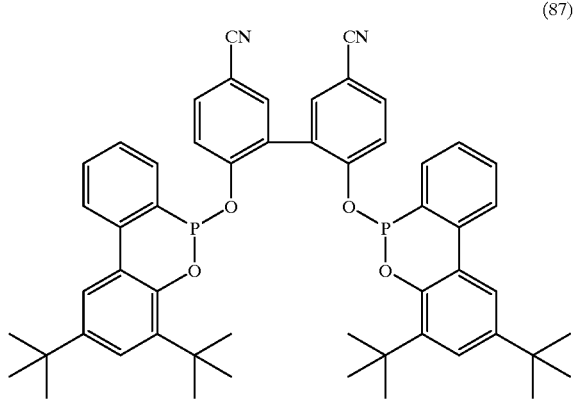
(87)
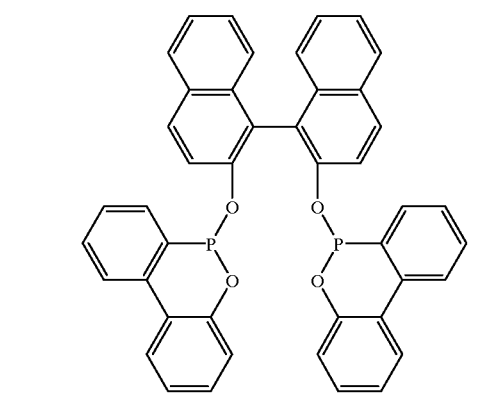
(88)
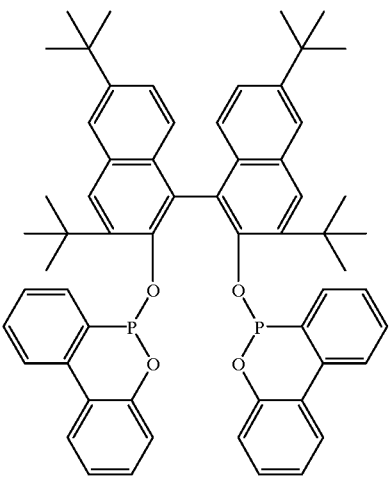
(89)
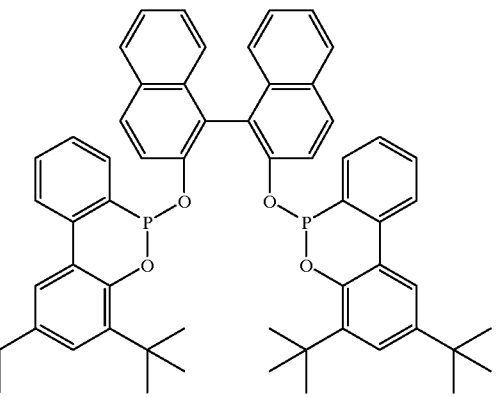
(90)
(91)
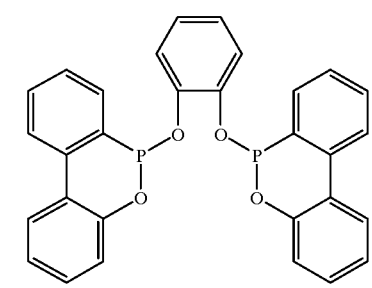
(92)

(93)
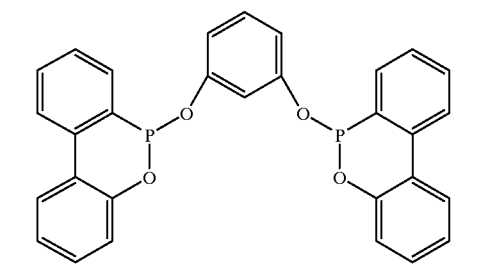
(94)
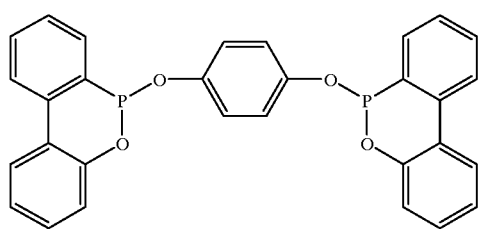
(95)
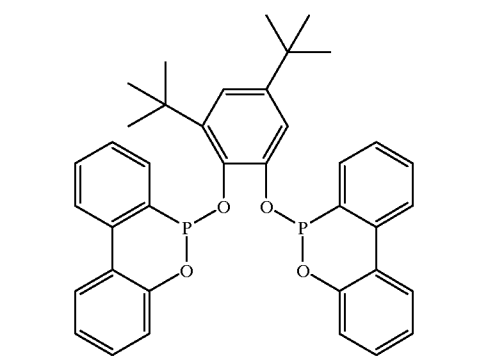
(96)
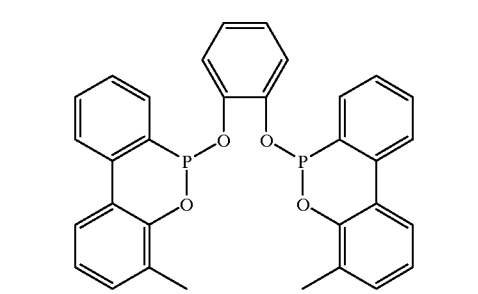
(97)
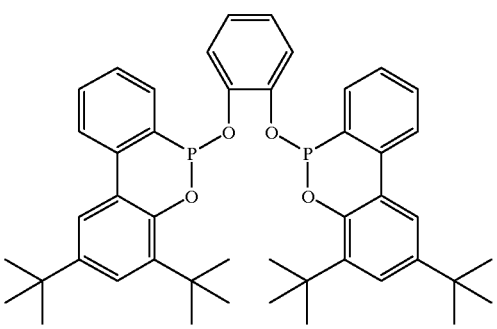
(98)
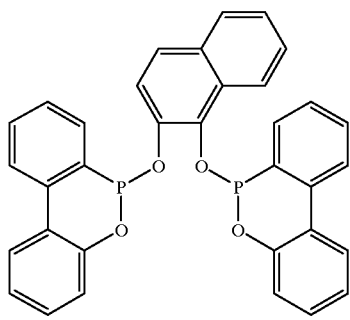
(99)
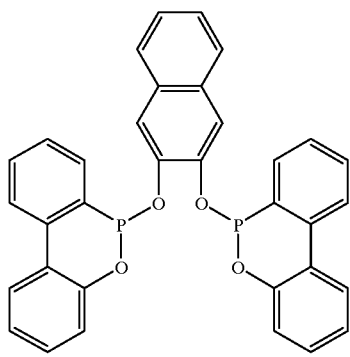
(100)
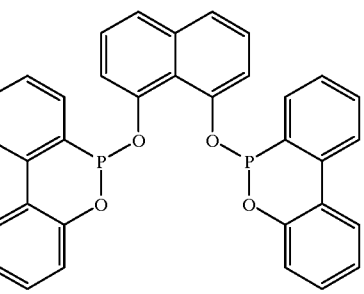
(101)
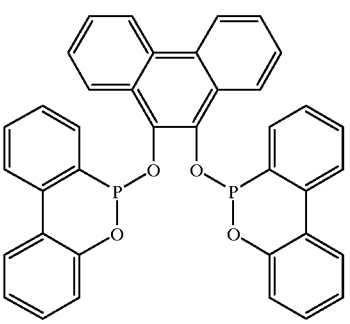

(102)
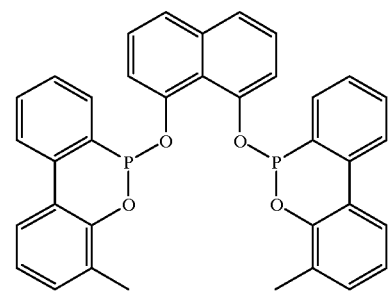
(103)
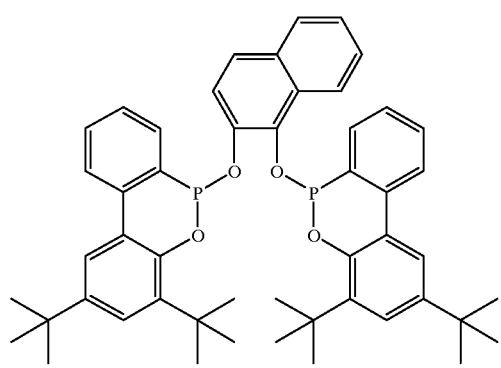
(104)
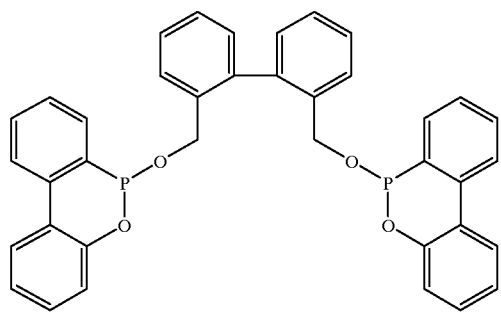
(105)
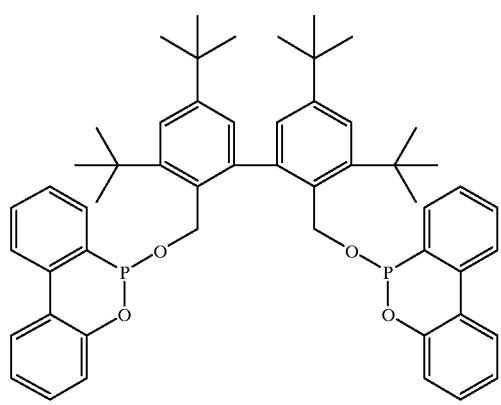
(106)
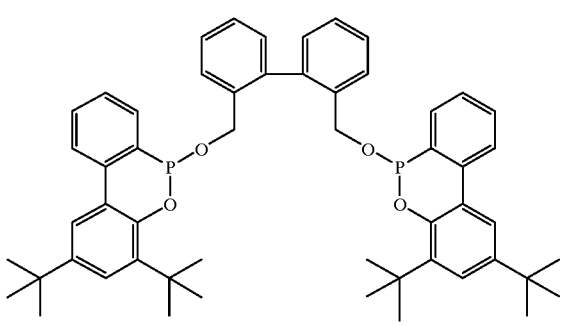
(107)
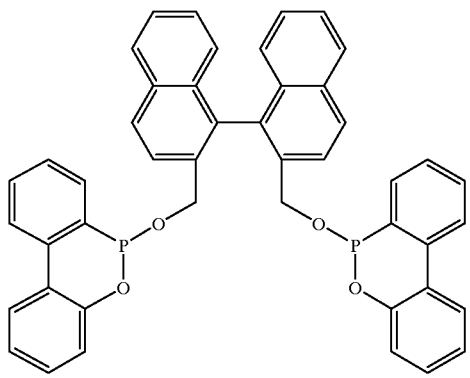
(108)
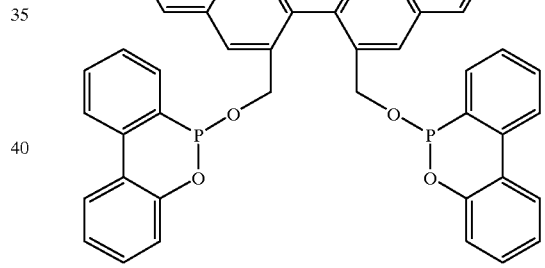
(109)
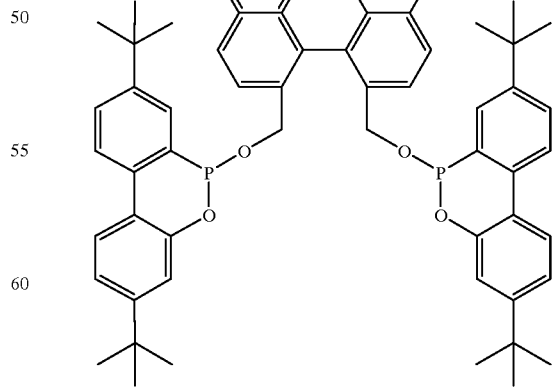

(110)
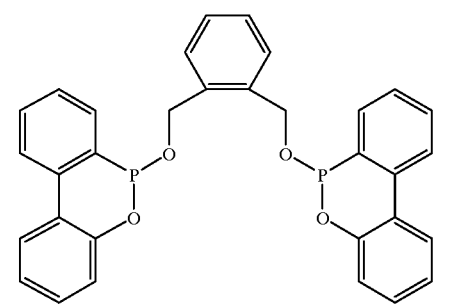
(111)
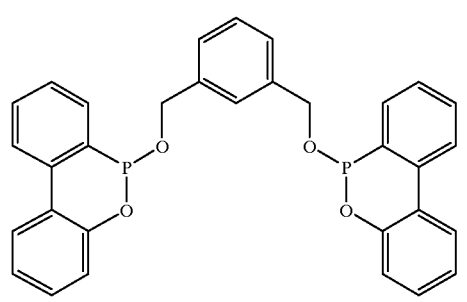
(112)
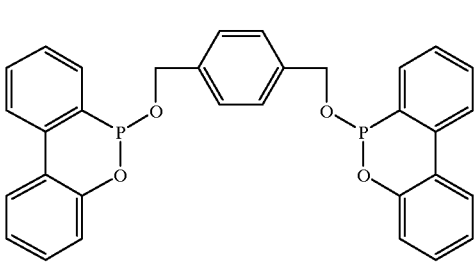
(113)
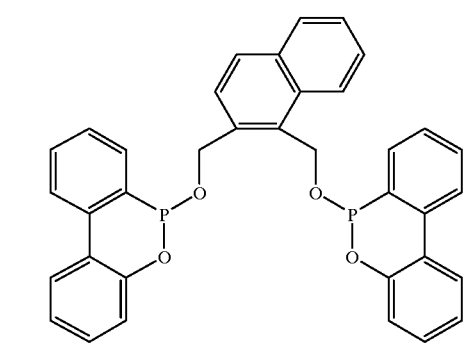
(114)
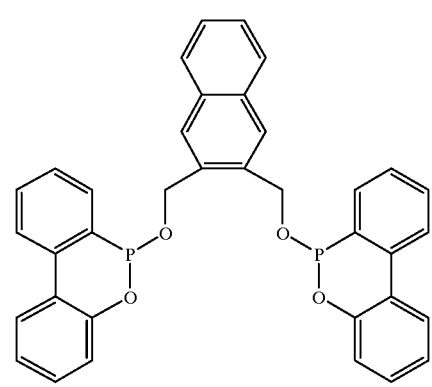
(115)
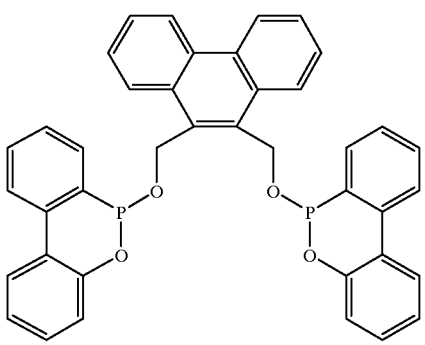
(116)
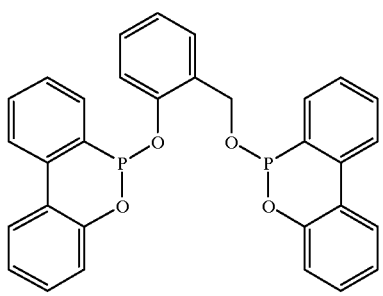
(117)
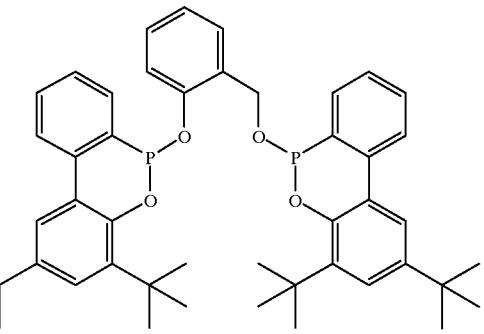
(118)
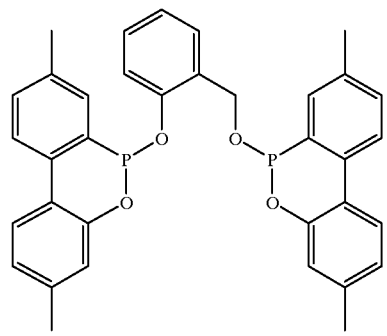

(119)
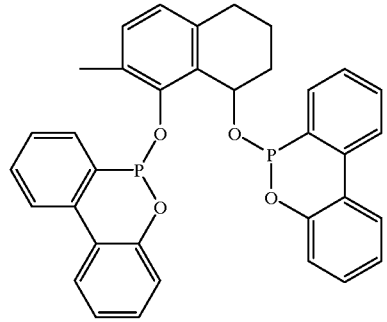
(123)
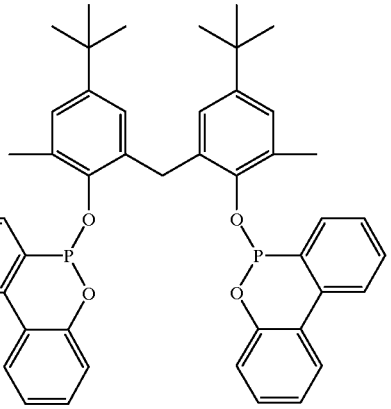
(120)
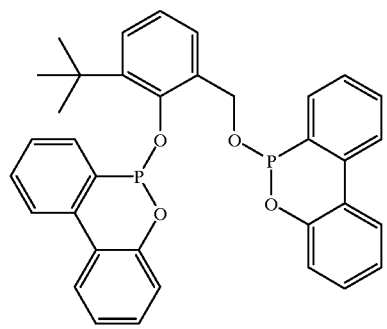
(124)
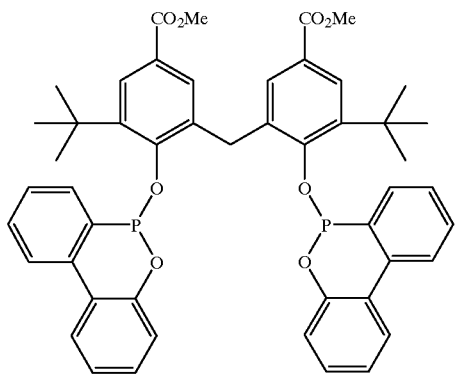
(121)
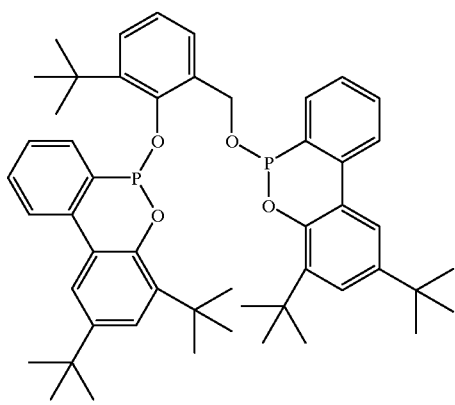
(125)
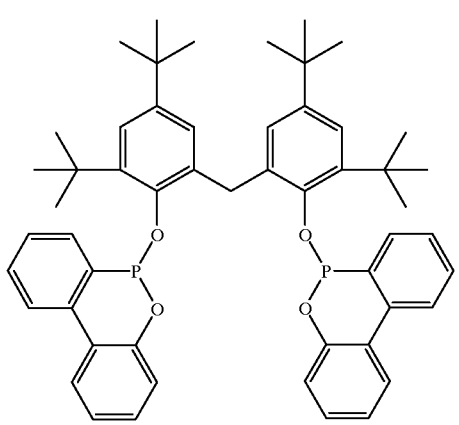
(122)
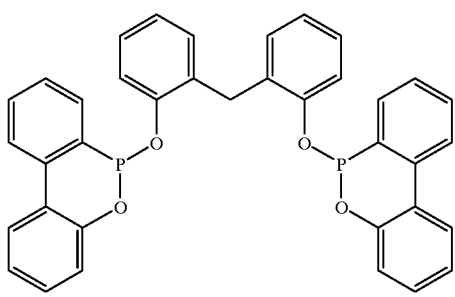
(126)
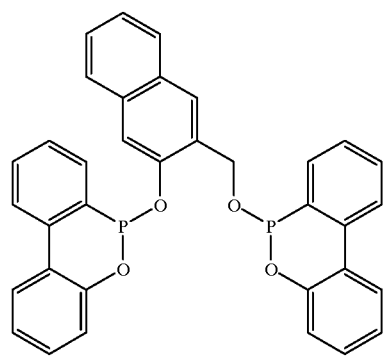

(127)

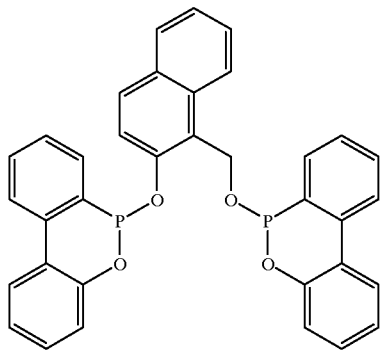

(V')

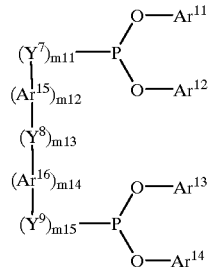

wherein each of $Ar^{11}$, $Ar^{12}$, $Ar^{13}$ and $Ar^{14}$ is a substituted or unsubstituted aromatic hydrocarbon group, each of $Ar^{15}$ and $Ar^{16}$ is a substituted or unsubstituted bivalent aromatic hydrocarbon group, each of $Y^7$, $Y^8$ and $Y^9$ is a substituted or unsubstituted bivalent organic group which is not an aromatic hydrocarbon group, and each of m11, m12, m13, m14 and m15 is 0 or a positive integer.

In the bidentate non-cyclic phosphonite compound represented by the general formula (V) to be used in the present invention, each of $X^8$, $X^9$, $X^{10}$ and $X^{11}$ is a substituted or unsubstituted hydrocarbon group, and no bonding is formed among these. The hydrocarbon group may be a $C_{1-30}$ alkyl group which may be branched, a cycloalkyl group, an alkenyl group which may be branched, or a $C_{6-30}$ aryl group. The alkyl group may, for example, be a methyl group, an ethyl group, a propyl group, a butyl group or an octyl group. The cycloalkyl group may, for example, be a cyclopropyl group, a cyclopentyl group or a cyclohexyl group. The alkenyl group may, for example, be a vinyl group, an allyl group or a 1-cyclohexenyl group. The aryl group may, for example, be a phenyl group, a 1-naphthyl group or a 2-naphthyl group.

As the bivalent organic group represented by $Q^6$, a bivalent organic group having no oxygen atom at the terminals, is employed, and a substituted or unsubstituted bivalent hydrocarbon group may, for example, be mentioned.

The above-mentioned substituted or unsubstituted bivalent hydrocarbon group represented by $Q^6$, may, for example, be a $C_{1-30}$ alkylene group, a cycloalkylene group, an alkenylene group, a $C_{6-30}$ arylene group, or an organic group comprising the plurality of them.

The substituent for each of hydrocarbon groups represented by $X^8$, $X^9$, $X^{10}$, $X^{11}$ and $Q^6$ may, for example, be a $C_{1-30}$, preferably $C_{1-8}$, alkyl group, a cycloalkyl group, a $C_{6-22}$, preferably $C_{6-14}$, aryl group, a $C_{1-30}$, preferably $C_{1-8}$, alkoxy group, a $C_{7-30}$ alkyl aryl group, an aryl alkyl group, an acyl group, a carbonyloxy group, an oxycarbonyl group, a sulfonyl group, a sulfinyl group, a silyl group, an alkylamino group, a hydroxyl group, an amino group, a cyano group, a nitro group or a halogen atom. As the substituent, the alkyl group may, for example, be a methyl group, an ethyl group, a propyl group, a butyl group or an octyl group, the cycloalkyl group may, for example, be a cyclopropyl group, a cyclopentyl group or a cyclohexyl group, the alkenyl group may, for example, be a vinyl group, an allyl group or a 1-cyclohexenyl group, and the aryl group may, for example, be a phenyl group, a 1-naphthyl group or a 2-naphthyl group. From 1 to 5 such substituents may be substituted on each of hydrocarbon groups of $X^8$, $X^9$, $X^{10}$, $X^{11}$ and $Q^6$, and the substituents may be the same or different.

Among the compounds represented by the general formula (V), a non-cyclic phosphonite compound represented by the following general formula (V') wherein $X^8$, $X^9$, $X^{10}$ and $X^{11}$ are aromatic hydrocarbon groups, is preferred:

In the general formula (V'), the aromatic hydrocarbon group represented by each of $Ar^{11}$, $Ar^{12}$, $Ar^{13}$ and $Ar^{14}$, is a substituted or unsubstituted $C_{6-30}$ aryl group, the bivalent aromatic hydrocarbon group represented by each of $Ar^{15}$ and $Ar^{16}$ is a substituted or unsubstituted $C_{6-30}$ arylene group, and the bivalent organic group represented by each of $Y^7$, $Y^8$ and $Y^9$ is a substituted or unsubstituted $C_{1-5}$ alkylene group, a carbonyl group, an imino group, a carbonylimino group, a substituted or unsubstituted sulfur atom, or a substituted or unsubstituted silylene group. The substituent for each of $Ar^{11}$, $Ar^{12}$, $Ar^{13}$, $Ar^{14}$, $Ar^{15}$, $Ar^{16}$, $Y^7$, $Y^8$ and $Y^9$, may, for example, be a $C_{1-30}$, preferably $C_{1-8}$, alkyl group, a cycloalkyl group, a $C_{6-22}$ preferably $C_{6-14}$, aryl group, a $C_{1-30}$, preferably $C_{1-8}$, alkoxy group, a $C_{7-30}$ alkyl aryl group, an aryl alkyl group, an acyl group, a carbonyloxy group, an oxycarbonyl group, a sulfonyl group, a sulfinyl group, a silyl group, an alkylamino group, a hydroxyl group, an amino group, a cyano group, a nitro group or a halogen atom. From 1 to 5 such substituents may be substituted on each of hydrocarbon groups of $Ar^{11}$, $Ar^{12}$, $Ar^{13}$ and $Ar^{14}$, from 1 to 4 such substituents may be substituted on each of hydrocarbon groups of $Ar^{15}$ and $Ar^{16}$, from 1 to 2 such substituents may be substituted on each of hydrocarbon groups of $Y^7$, $Y^8$ and $Y^9$, and the substituents may be the same or different. Further, substituents in $Ar^{15}$, $Ar^{16}$, $Y^7$, $Y^8$ and $Y^9$ may together form a bond with each other.

Specifically, each of $Ar^{11}$, $Ar^{12}$, $Ar^{13}$ and $Ar^{14}$ may, for example, be a phenyl group, a 2,4-di-t-butylphenyl group, a 2-t-butyl-4-methoxyphenyl group, a 2-cyclohexyl-4-methylphenyl group, a 4-cyano-2-methoxyphenyl group, a 2,4-dichlorophenyl group, a 1-naphthyl group, a 2-naphthyl group, a 9-phenanthryl group or a 3,6-di-t-butyl-2-naphthyl group. Among these, as each of $Ar^{11}$, $Ar^{12}$, $Ar^{13}$ and $Ar^{14}$, a phenyl group, a 2,4-di-t-butylphenyl group, a 1-naphthyl group, a 2-naphthyl group and a 3,6-di-t-butyl-2-naphthyl group are preferred.

Further, each of m11, m12, m13, m14 and m15 is preferably 0 or 1.

The bivalent group represented by $(Y^7)m11$-$(Ar^{15})m12$-$(Y^8)m13$-$(Ar^{16})m14$-$(Y^9)m15$ is a bivalent group having no oxygen atom at the terminals. Specifically, it may, for example, be a methylene group, an ethylene group, a 1,3-propylene group, a 1,4-butylene group, a 1,5-pentylene group, a 1,2-phenylene group, a 1,3-phenylene group, a 1,4-phenylene group, a 1,2-naphthylene group, a 2,3- naphthylene group, a 2,2'-biphenylene group, a 4,5-anthrylene group, a 4,5-phenanthrylene group, a 3,3'-dimethyl-2,2'-biphenylene group, a 3,3',5,5'-tetra-t-butyl-2,2'-biphenylene group, a 2,2'-(1,1'-binaphthylene) group, a 1,1'-(2,2'-binaphthylene) group, a 3,3',6,6'-tetra-t-butyl-2,2'-(1,1'-binaphthylene) group, a 3,3'-dimethyl-2,2'-(1,1'-binaphthylene) group, a 1,2-dimethylenebenzene group, a 1,3-dimethylenebenzene group, a 1,4-dimethylenebenzene group, a 1,2-dimethylenenaphthalene group, a 2,3-dimethylenenaphthalene group, a 2,2'-dimethylenebiphenyl group, a 3,3',5,5'-tetra-t-butyl-2,2'-dimethylenebiphenyl group, a 3,3'-di-t-butyl-5,5'-dimethoxy-2,2'-dimethylenebiphenyl group, a 2,2'-dimethylene-(1,1'-binaphthalene) group, a 2,2'-dimethylene-3,3',6,6'-tetra-t-butyl-(1,1'-binaphthalene) group, a 4,5-dimethylenephenanthrene group, 2-methylenephenyl group or a 2-t-butyl-6-methylenephenyl group.

Representative examples of the bidentate non-cyclic phosphonite compound represented by the general formula (V') will be given below.

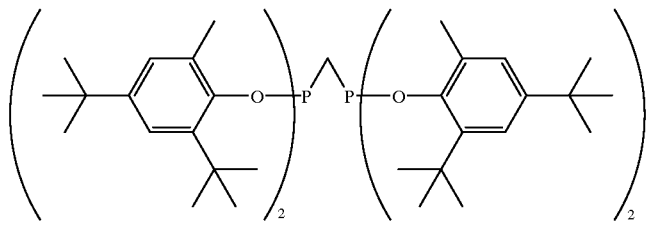

(128)

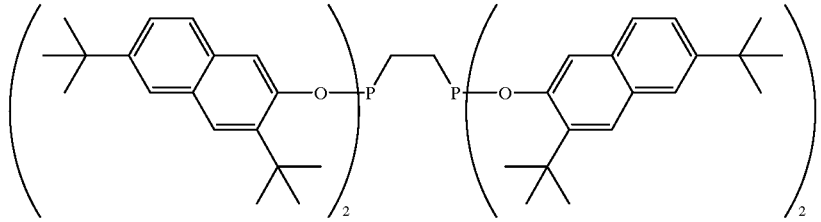

(129)

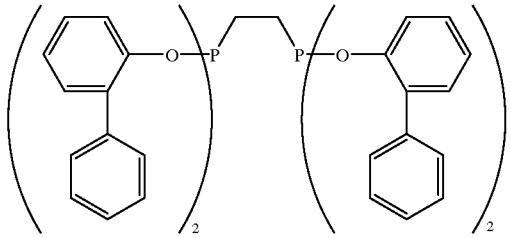

(130)

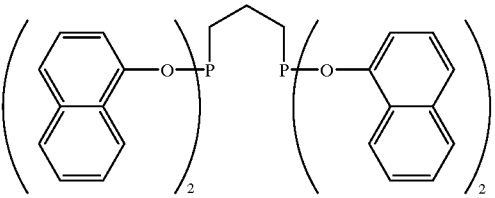

(131)

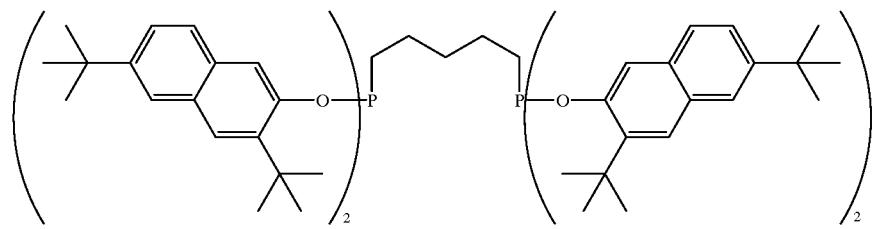

(132)

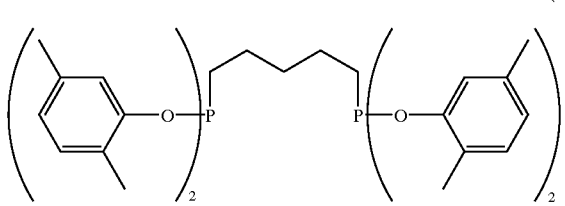

(133)

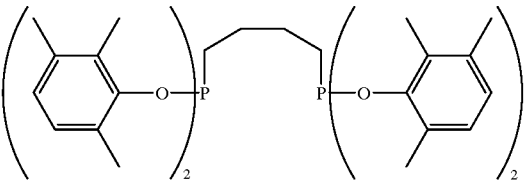

(134)

-continued
(135)
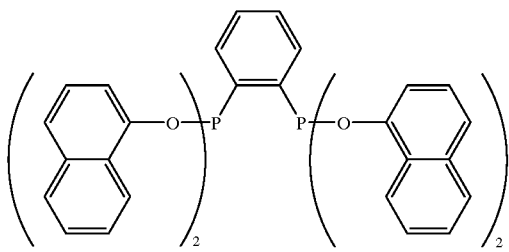
(136)
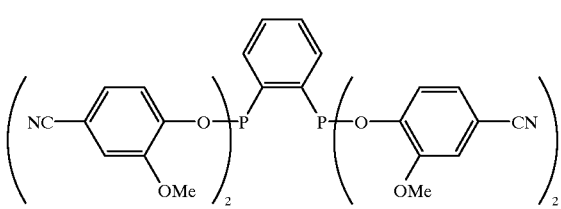
(137)
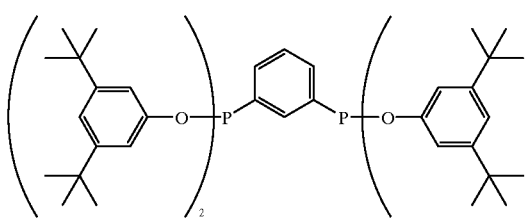
(138)
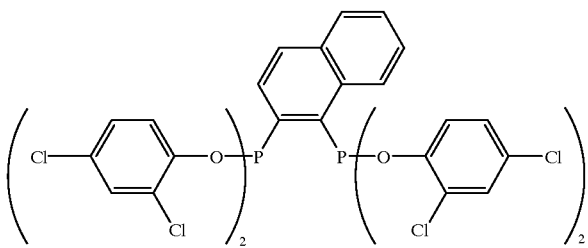
(139)
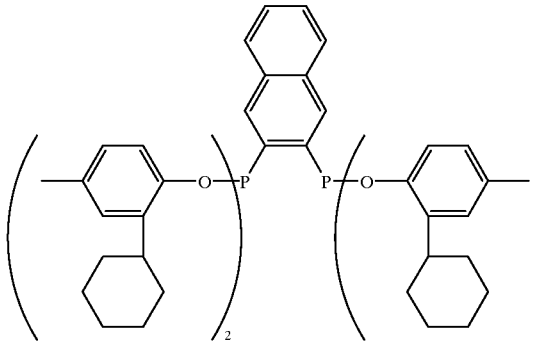
(140)
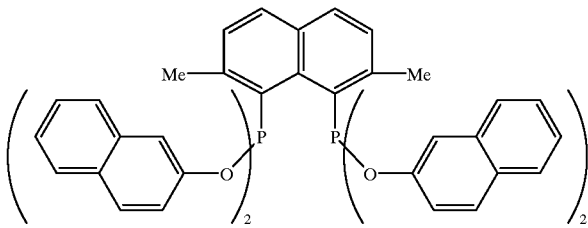
(141)
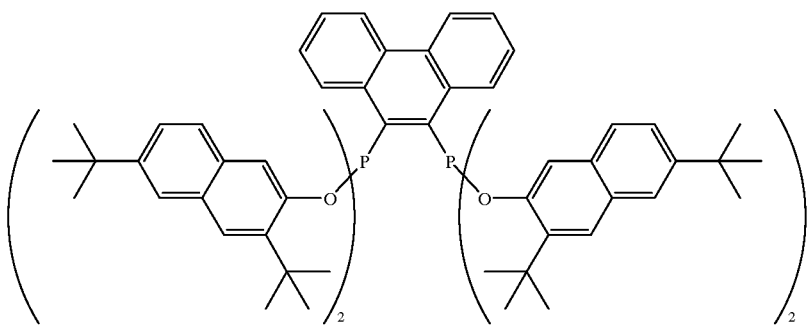
(142)
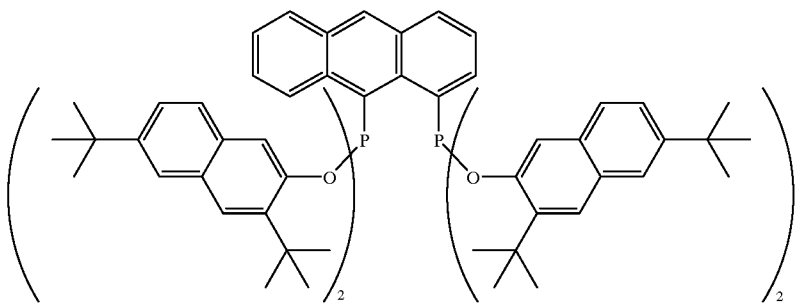

-continued
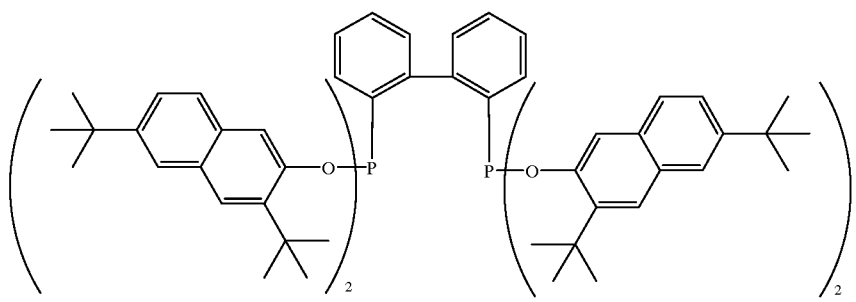
(143)
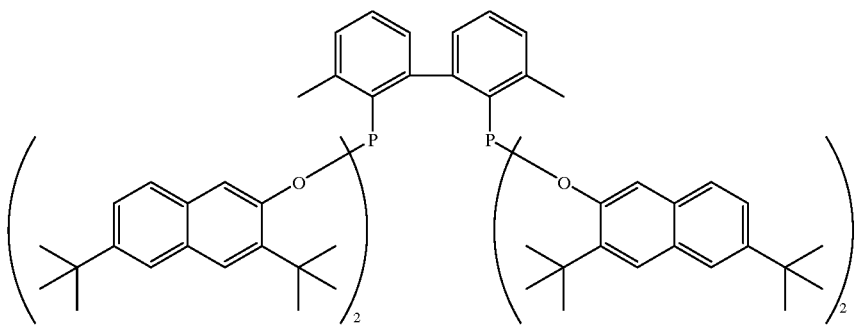
(144)
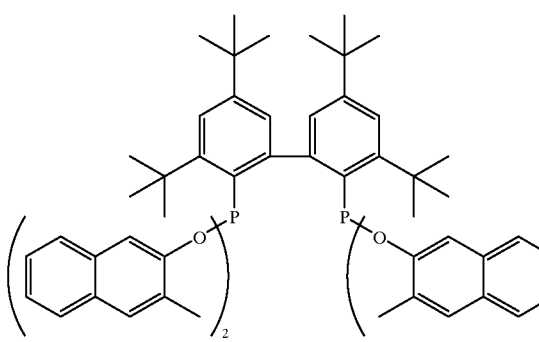
(145)
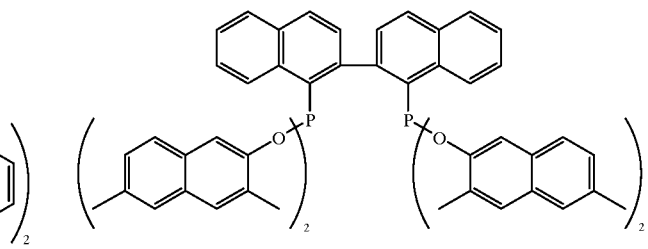
(146)
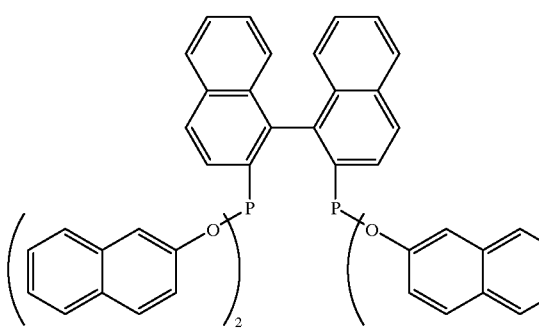
(147)
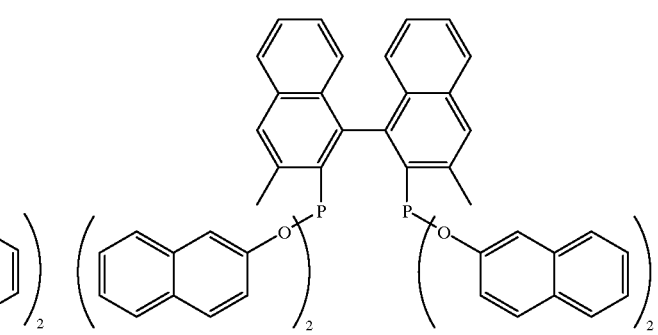
(148)

(149)
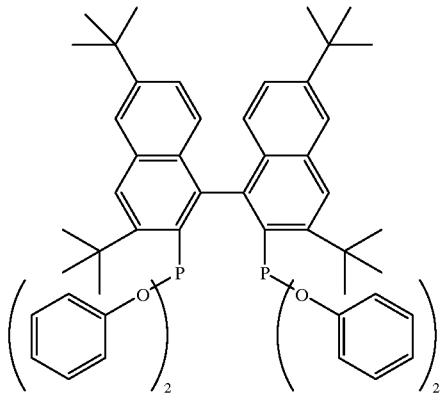
(150)
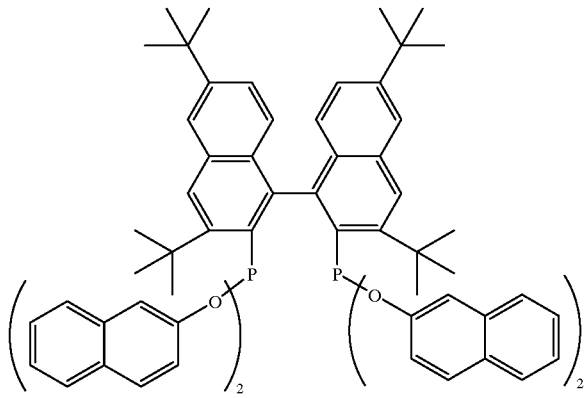
(151)
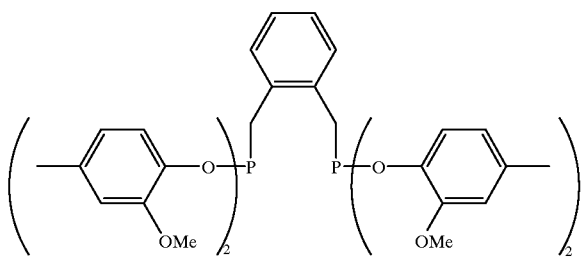
(152)
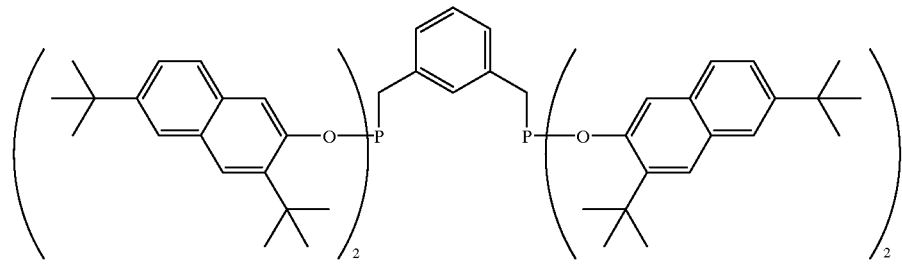
(153)
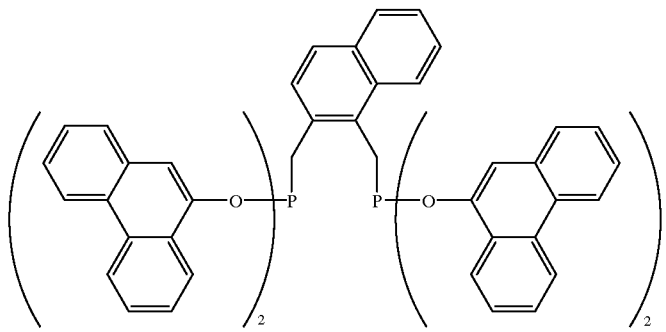

-continued
(154)
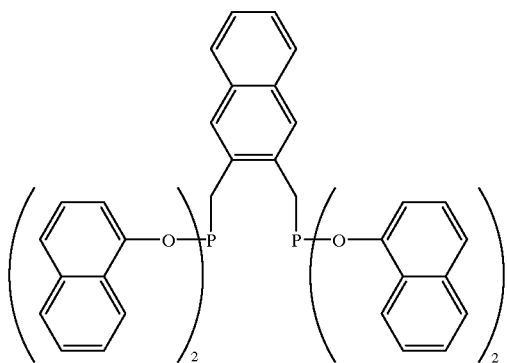
(155)
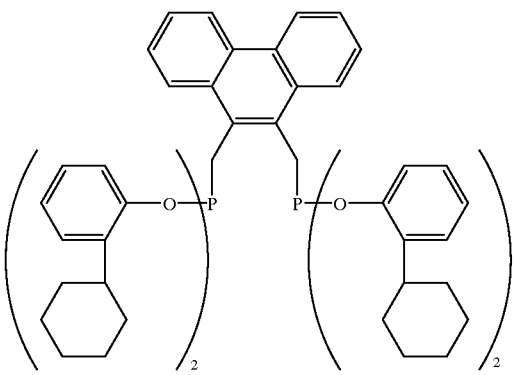
(156)
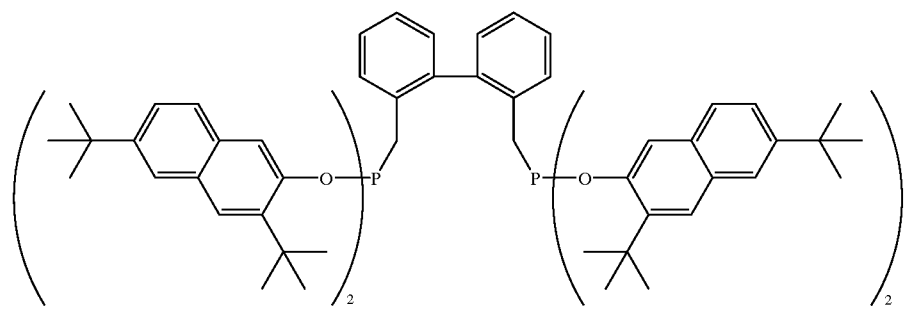
(157)
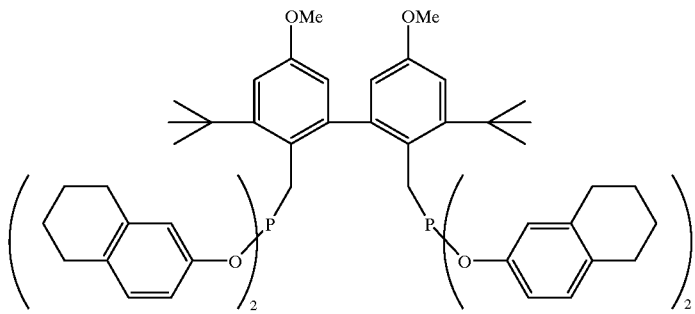
(158)
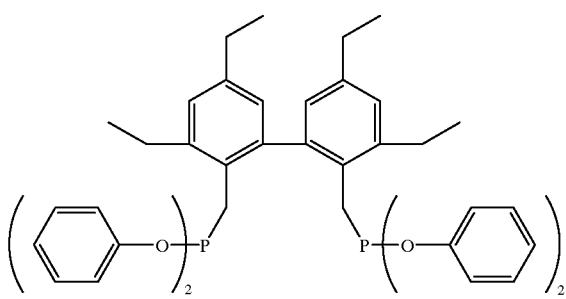
(159)
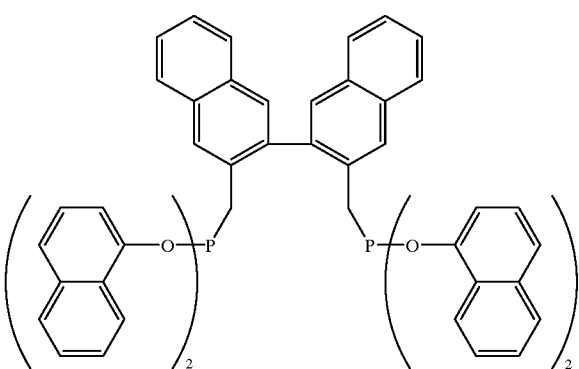

-continued
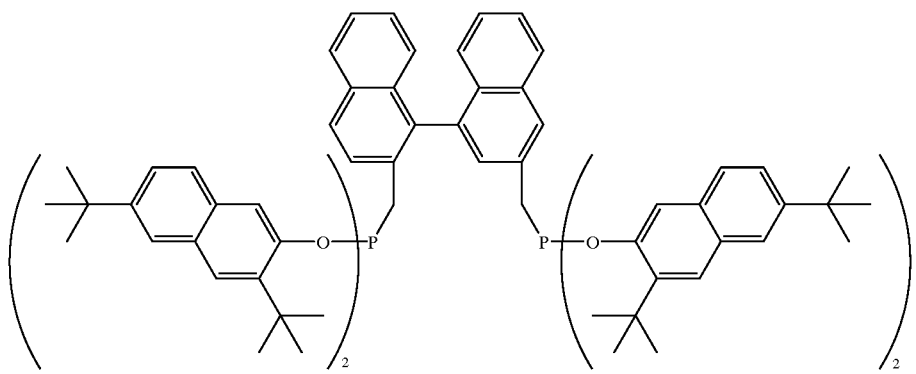
(160)
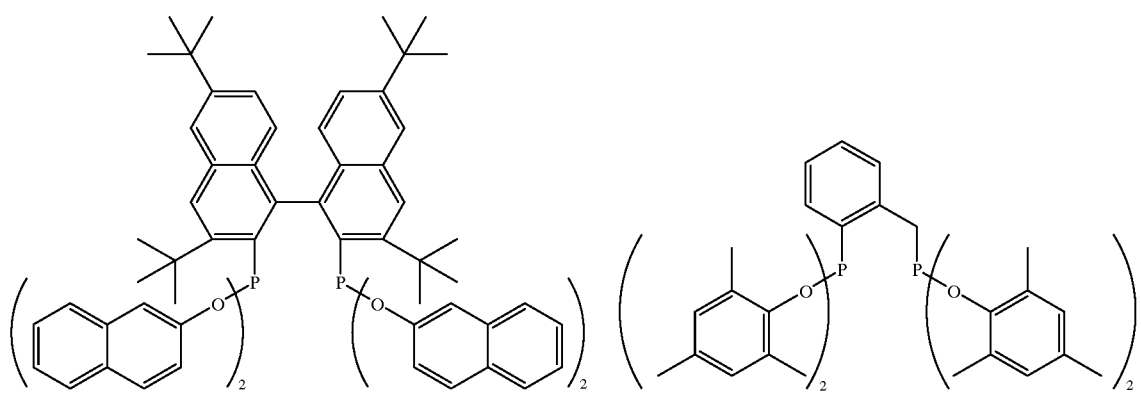
(161) (162)
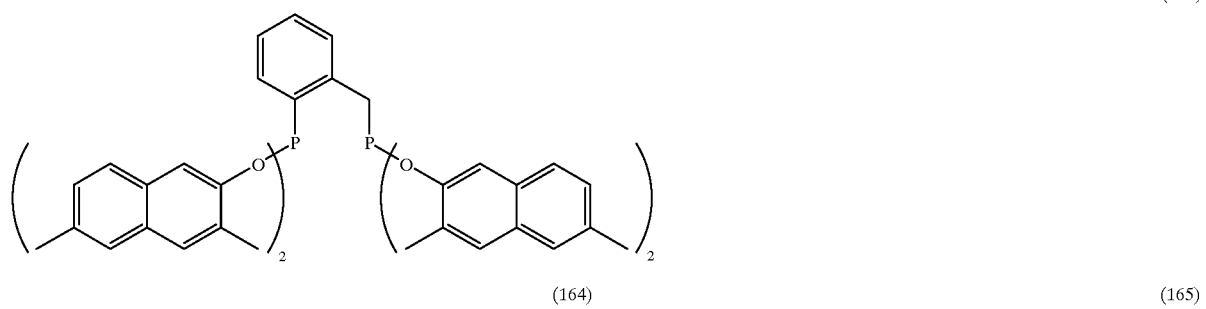
(163)
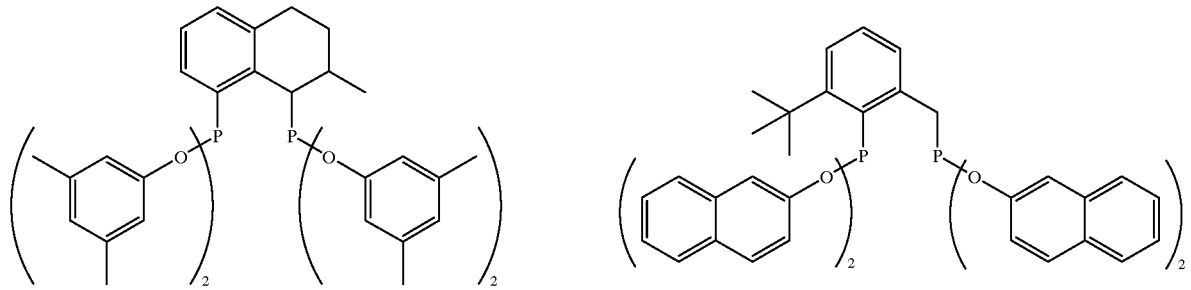
(164) (165)

(166)

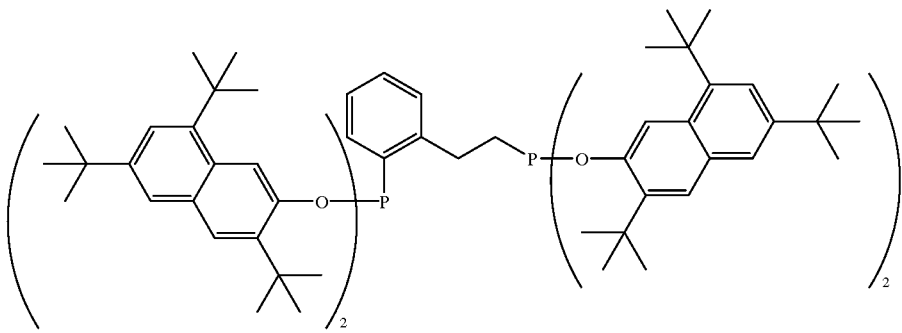

(167)

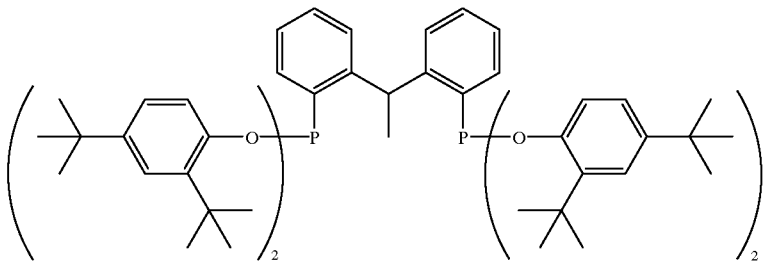

(168)

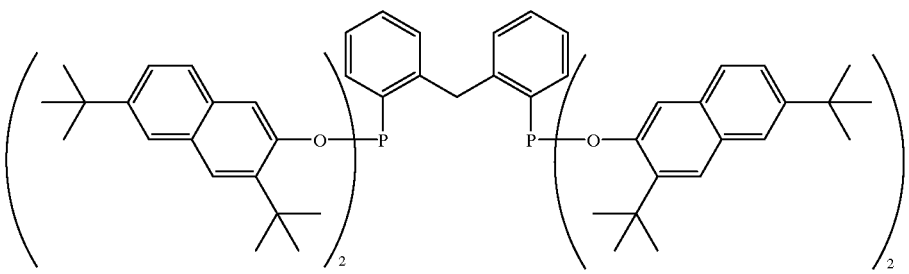

(169)

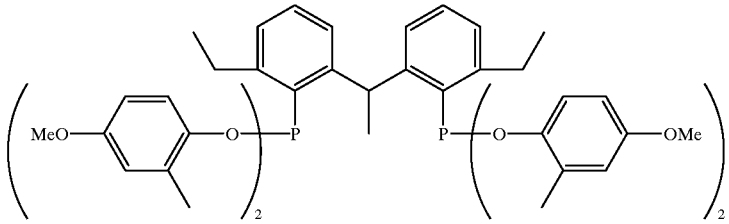

The hydroformylation process by the present invention is characterized by using a cyclic or non-cyclic, particularly a bidentate cyclic or bidentate non-cyclic, phosphonite compound having a certain specific structure, represented by any one of the general formulae (I) to (V), instead of the phosphine compound or the phosphite compound, which has conventionally been used as the phosphorus ligand. The phosphonite compound is a compound in which among three substituents for the phosphorus atom, only one substituent has a P—C bond, and the other two substituents have P—O bonds. The structure of the compound has a important impact on the production ratio of the product of the hydroformylation reaction. Further, in the case of the phosphonite compound, such a fact that both an oxygen atom and a carbon atom which are significantly different in electronegativity, are bonded to the phosphorus atom, has an impact on the electrical state of the phosphorus atom. The environmental differences can be observed by the difference in the chemical shift in measurement by $^{31}P$ nuclear magnetic resonance spectrophotometry ($^{31}P$ NMR). Further, among the phosphonite compounds having a certain specific structure of the present invention, particularly the bidentate cyclic phosphonite compound represented by the general formula (IV') or the bidentate non-cyclic phosphonite compound represented by the general formula (V') has a high stability as the ligand, and accordingly, the reaction rate will be improved, such being advantageous.

In the hydroformylation reaction employing the above-mentioned specific phosphonite compound of the present invention, as compared with the case where the conventional phosphine compound or phosphonite compound is employed, a high reaction activity and a high selectivity of a straight chain isomer as a product can be obtained, and the reduction reaction of the olefine as a side-reaction can be suppressed. Particularly, the reduction reaction of the olefine as a side-reaction can significantly be suppressed, which is considered to be attributable to the fact that the electronic state of the phosphorus atom in the above-mentioned phosphonite compound is significantly different from the electronic state in the conventional phosphine compound or phosphite compound, as mentioned above. Further, it is considered that as the above-mentioned phosphonite compound has one P—C bond and two P—O bonds, the steric effect is different from the ligand such as a phosphine or a phosphite, and as a result, the reaction activity, the selectivity and the olefin reduction property, which are different from the conventional ligand, can be obtained.

The olefinic compound to be used as the reaction starting material in the hydroformylation reaction in the present invention, is not particularly limited so long as it is an organic compound having at least one olefinic double bond in its molecule. Specifically, it may, for example, be ethylene, propylene, butene, butadiene, pentene, hexene, hexadiene, octene, octadiene, decene, hexadecene, octadecene, icosene, docosene, styrene, α-methylstyrene, cyclohexene, a lower olefin mixture such as a propylene-butene mixture, a n-butene-2-butene-isobutyrene mixture or a n-butene-2-butene-isobutyrene-butadiene mixture, an olefinic hydrocarbon such as a mixture of olefinic oligomer isomers such as dimer to tetramer of a lower olefin such as propylene, n-butene or isobutylene, or a hetero-atom group-substituted olefin such as acrylonitrile, allylalcohol, 1-hydroxy-2,7-octadiene, 3-hydroxy-1,7-octadiene, oleyl alcohol, 1-methoxy-2,7-octadiene, methyl acrylate, methyl methacrylate or methyl oleate.

The Group VIII metal compound to be used in the present invention is a compound of a metal selected from metals of Group VIII, i.e. rhodium, cobalt, platinum, iridium, palladium and ruthenium, and a mixture thereof. Preferred metal is rhodium, cobalt or platinum, and particularly preferred is rhodium. The rhodium compound may, for example, be an inorganic salt or an organic salt of rhodium such as rhodium chloride, rhodium nitrate, rhodium acetate, rhodium formate, sodium chlororhodate or potassium chlororhodate, a rhodium metal supported on a support such as alumina, silica or activated carbon, a chelate compound of rhodium such as rhodium dicarbonylacetylacetonate, or a carbonyl complex compound of rhodium such as tetrarhodium dodecacarbonyl, hexarhodium hexadecacarbonyl, $\mu,\mu'$-dichlororhodium tetracarbonyl, $[Rh(OAc)(COD)]_2$ (wherein Ac represents an acetyl group, and COD 1,5-cyclooctadiene), or $[Rh(\mu\text{-S-t-Bu})(CO)_2]_2$. Another Group VIII metal compound may, for example, be a cobalt compound such as dicobalt octacarbonyl or cobalt stearate, a platinum compound such as platinic acid, sodium hexachloroplatinate or potassium platinate, an iridium compound such as iridium trichloride or iridium carbonyl, or a ruthenium compound such as ruthenium trichloride or tetraamminehydroxochlororuthenium chloride. Further, the addition mode of the Group VIII metal compound is not particularly limited.

The amount of the Group VIII metal compound is not particularly limited, and there is a limit from the viewpoint of the catalytic activity and the economical feasibility. It is usually selected so that the concentration in the hydroformylation reaction zone is within a range of from 0.05 mg to 5 g, preferably from 0.5 mg to 1 g, per litter of the reaction solvent, as calculated as the metal atom.

In the present invention, the phosphonite compound may be used as preliminarily permitted to form a complex with the above-mentioned Group VIII metal compound. The Group VIII metal complex containing the phosphonite compound can readily be prepared by a conventional method for forming a complex from the Group VIII metal compound and the above-mentioned phosphonite compound. In some cases, the Group VIII metal compound and the above phosphonite compound may be supplied to the hydroformylation reaction zone to form the complex there.

In the present invention, the amount of the phosphonite compound is not particularly limited, and it is selected usually within a range of from about 0.001 to 1,000 mols, preferably from 0.1 to 200 mols, particularly preferably from 0.3 to 20 mols, per mol of the Group VIII metal.

Use of a reaction solvent is not essential for the hydroformylation reaction. However, a solvent inert to the hydroformylation reaction may be used as the case requires. Specifically, the preferred solvent may, for example, be an aliphatic hydrocarbon such as hexane, heptane or octane, an aromatic hydrocarbon such as toluene, xylene or dodecylbenzene, a ketone such as acetone, diethyl ketone or methyl ethyl ketone, an ether such as tetrahydrofuran or dioxane, an ester such as ethylacetate or di-n-octylphthalate, or a high boiling component produced as a by-product at the time of the hydroformylation reaction, such as a condensation product of an aldehyde. The olefinic compound itself may be used as the solvent.

The reaction conditions for the hydroformylation reaction in the present invention may be the commonly employed reaction conditions. The reaction temperature is selected usually within a range of from 15 to 200° C., preferably from 50 to 150° C. The reaction pressure is selected usually within a range of from atmospheric pressure to 200 atm, preferably from 5 to 100 atm, particularly preferably from 5 to 50 atm. The molar ratio of hydrogen to carbon monoxide ($H_2$/CO) is selected usually within a range of from 10/1 to 1/10, preferably from 1/1 to 6/1.

The hydroformylation reaction can be carried out by either of a continuous system or a batch system, for example, in an agitation type reactor or a bubbling column type reactor. Further, the separation of the formed aldehydes from the catalyst, can be carried out by a known method such as distillation, and the separated catalyst liquid may be used to further conduct the hydroformylation reaction of the olefinic compound. Further, when the olefinic compound is continuously converted to aldehydes, a part or whole of the resulting aldehydes is separated, and the residual reaction liquid may be continuously recycled to the hydroformylation reactor.

Now, the present invention will be described in further detail with reference to Examples. However, it should be understood that the present invention is by no means restricted to such specific Examples.

EXAMPLE 1

Into an up and down stirring type stainless steel autoclave having an internal capacity of 200 ml, 55 ml of toluene as a solvent, 5 ml of heptane as an internal standard, and 39.4 mg of $[Rh(OAc)(COD)]_2$ and 1.0 mol per mol of rhodium of phosphonite compound (2) as the ligand were charged under a nitrogen atmosphere, and then the autoclave was sealed. The interior of the autoclave was completely replaced by nitrogen gas, then the pressure was reduced, and 4.50 g of propylene was injected thereto. The temperature was raised to 70° C., and a synthesis gas ($H_2$/CO) was injected to the autoclave so that the total pressure became 10.0 atm, to initiate the reaction. The pressure in the autoclave to be used for the reaction was kept at a certain pressure until the completion of the reaction, by supplementing a synthesis gas through an automatic pressure regulator, and the reaction was carried out for 1.0 hour. After the completion of the reaction, the reactor was cooled to room temperature. The gas phase and the liquid phase in the autoclave were subjected to the analyses of the respective components by means of gas chromatography, quantitative analyses of the formed aldehydes, unreacted propylene, propane as a reduction reaction product, etc., were carried out, and the reaction activity, the n/i ratio, the yield of aldehydes and the hydrogenation ratio ere obtained. The results are shown in Table 1.

EXAMPLES 2 to 10

The reaction was carried out in the same manner as in Example 1, except that the ligand, the ligand/Rh ratio and the reaction time were as shown in Table 1. The results are shown in Table 1.

TABLE 1

| Ex. | Ligand | Ligand/Rh ratio (mol/mol) | Reaction time (hr.) | Activity *1 | n/i ratio *2 | Yield of aldehydes (%) | Hydrogenation ratio (%) *3 |
|---|---|---|---|---|---|---|---|
| 1 | (2) | 1.0 | 1.0 | 3.42 | 1.3 | 100 | 0.19 |
| 2 | (2) | 4.0 | 1.0 | 5.92 | 2.0 | 98.2 | 0.15 |
| 3 | (3) | 1.0 | 0.7 | >15.6 | 1.1 | 100 | 0.22 |
| 4 | (3) | 4.0 | 1.5 | 3.79 | 1.5 | 100 | 0.16 |
| 5 | (3) | 8.0 | 4.0 | 1.45 | 1.6 | 97.4 | 0.13 |
| 6 | (23) | 4.0 | 1.85 | 2.71 | 1.1 | 100 | 0.15 |
| 7 | (39) | 4.0 | 1.7 | 3.95 | 1.0 | 99.7 | 0.06 |
| 8 | (51) | 4.0 | 0.9 | 2.08 | 1.8 | 100 | 0.10 |
| 9 | (52) | 4.0 | 2.4 | 3.60 | 1.6 | 98.9 | 0.11 |
| 10 | (53) | 4.0 | 0.8 | 3.50 | 1.7 | 98.8 | 0.03 |

*1 Activity = mol-Aldehyde products/l·hr
*2 n/i ratio = (mol of produced n-butyraldehyde)/(mol of produced isobutyl aldehyde)
*3 Hydrogenation ratio = yield of produced propane The structures of the phosphonite compounds used in Examples 1 to 10, are as follows.

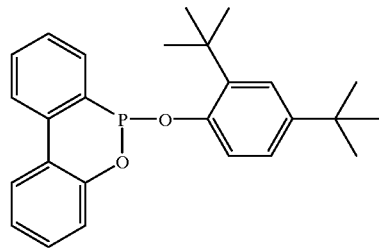

(2)

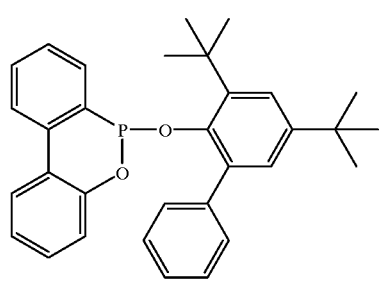

(3)

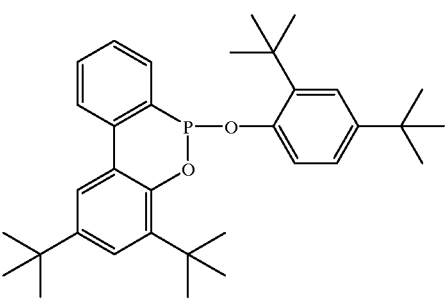

(23)

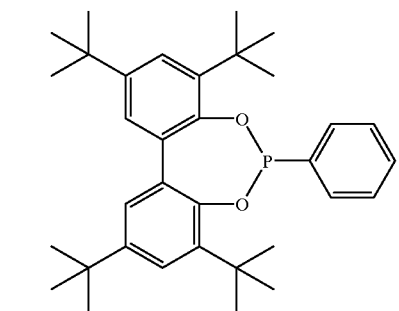

(39)

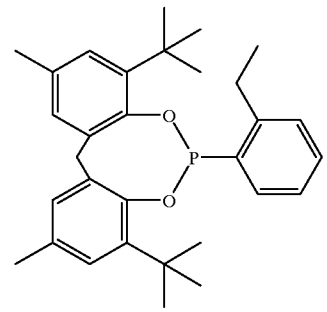

(51)

(52)

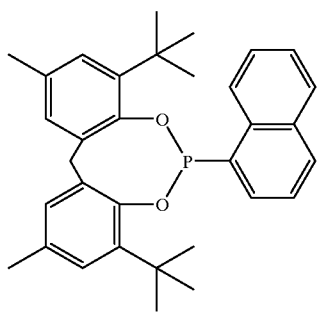

(53)

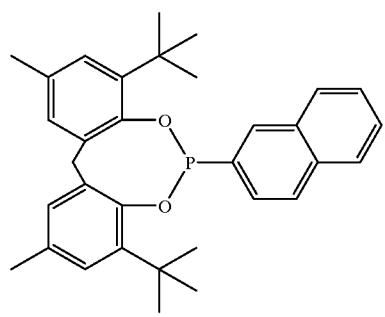

Reference Example 1
(Synthesis of Phophonite Compound (3))

The interior of a four neck flask of 200 ml equipped with a stirring apparatus, a reflux condenser and a thermometer, was replaced by nitrogen, and 2.655 g (11.3 mmol) of 6-chloro-6H-dibenzo[c,e][1,2]oxaphosphorin and about 12 ml of THF were put therein, followed by stirring and cooling to 0° C. While keeping the stirring, a solution having 3.182 g (11.2 mmol) of 2,4-di-t-butyl-6-phenylphenol and 2.396 g (23.7 mmol) of triethylamine dissolved in about 23 ml of THF, was dropwisely added to the solution over a period of 0.5 hour. After the dropwise addition, the stirring was carried out further for 1 hour. Then, by-product solid triethylamine hydrochloride was filtered off, and the solvent was distilled off from the filtrate, to obtain a residual solid. Further, by silica gel column chromatography, 2.236 g (23.7 mmol) of phosphonite compound (3) as a white solid was isolated. The yield was 41.5%. It was a colorless transparent liquid.

By using $^{1}$H, $^{13}$C and $^{31}$P nuclear magnetic resonance spectrophotometry (NMR; by using Unity 300 model manufactured by Barian), it was confirmed that the synthesized phosphonite compound (3) had a structure of the desired compound. Chemical shift values of each NMR are shown in Table 2.

TABLE 2

$^{31}$P NMR(δ, CDCl$_3$); 131.8
$^{1}$H NMR(δ, CDCl$_3$; intensity, multiplicity, coupling constant (J in Hz));
7.98(1H, d, 6.4 & 1.2), 7.87(1H, bdd, 8.1 & 0.5), TABLE 2-continued 7.49(1H, t, 5.6), 7.40–7.18(9H, m), 7.04(1H, d, 2.7),
6.46(1H, dd, 5.7 & 0.9), 6.42(1H, 0.7), 1.30(9H, s), 1.15(9H, s)
$^{13}$C NMR(δ, CDCl$_3$; multiplicity, coupling constant (J in Hz) );
149.8(d, 9.1), 149.5(d, 8.2), 145.2(d, 1.2), 141.3(d, 2.7),
141.2(d, 2.4), 134.8(d, 6.1), 132.2(s), 132.2(s),
132.0(s), 131.5(s), 131.4(s), 131.3(s), 131.2(s),
129.1(s), 128.5(s), 127.4(d, 0.6), 127.1(s), 127.1(s),
126.9(s), 124.4(s), 123.9(s), 123.2(s), 122.9(s),
121.4(d, 1.5), 35.3(s), 34.4(s), 31.5(s), 30.8(s)

$^{31}$P NMR: Chemical shift values based on phosphoric acid
$^{1}$H NMR: Chemical shift values based on TMS
$^{13}$C NMR: Chemical shift values based on TMS

EXAMPLE 11

Into an up and down stirring type stainless steel autoclave having an internal capacity of 200 ml, 55 ml of toluene as a solvent, 5 ml of heptane as an internal standard, and 39.4 mg of [Rh(OAc)(COD)]$_2$ and 4.0 mol per mol of rhodium of phosphonite compound (63) having the following structure as the ligand were charged under a nitrogen atmosphere, and then the autoclave was sealed. The interior of the autoclave was completely replaced by nitrogen gas, then the pressure was reduced, and 4.50 g of propylene was injected thereto. The temperature was raised to 70° C., and a synthesis gas (H$_2$/CO) was injected to the autoclave so that the total pressure became 10.0 atm, to initiate the reaction. The pressure in the autoclave to be used for the reaction was kept at a certain pressure until the completion of the reaction, by supplementing a synthesis gas through an automatic pressure regulator, and the reaction was carried out for 0.55 hour. After the completion of the reaction, the reactor was cooled to room temperature. The gas phase and the liquid phase in the autoclave were subjected to the analyses of the respective components by means of gas chromatography, quantitative analyses of the formed aldehydes, unreacted propylene, propane as a reduction reaction product, etc., were carried out, and the reaction activity, the n/i ratio, the yield of aldehydes and the hydrogenation ratio were obtained. The results are shown in Table 3.

(63)

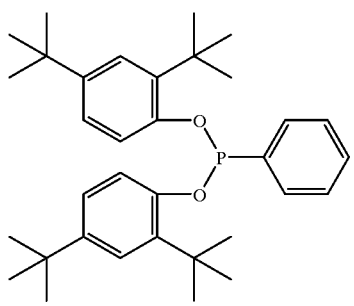

TABLE 3

| Ex. | Ligand | Ligand/Rh ratio (mol/mol) | Reaction time (hr.) | Activity *1 | n/i ratio *2 | Yield of aldehydes (%) | Hydrogenation ratio *3 (%) |
|---|---|---|---|---|---|---|---|
| 11 | (63) | 4.0 | 0.55 | >10.6 | 1.1 | 100 | 0.16 |

*1 Activity = mol-Aldehyde products/l·hr
*2 n/i ratio = (mol of produced n-butyraldehyde)/(mol of produced isobutyl aldehyde)
*3 hydrogenation ratio = yield of produced propane

EXAMPLE 12

Into an up and down stirring type stainless steel autoclave having an internal capacity of 200 ml, 55 ml of toluene as a solvent, 5 ml of heptane as an internal standard, and 39.4 mg of [Rh(OAc)(COD)]$_2$ and 1.0 mol per mol of rhodium of phosphonite compound (80) having the following structure as the ligand were charged under a nitrogen atmosphere, and then the autoclave was sealed. The interior of the autoclave was completely replaced by nitrogen gas, then the pressure was reduced, and 4.50 g of propylene was injected thereto. The temperature was raised to 70° C., and a synthesis gas (H$_2$/CO) was injected to the autoclave so that the total pressure became 10.0 atm, to initiate the reaction. The pressure in the autoclave to be used for the reaction was kept at a certain pressure until the completion of the reaction, by supplementing a synthesis gas through an automatic pressure regulator, and the reaction was carried out for 2.0 hours. After the completion of the reaction, the reactor was cooled to room temperature. The gas phase and the liquid phase in the autoclave were subjected to the analyses of the respective components by means of gas chromatography, quantitative analyses of the formed aldehydes, unreacted propylene, propane as a reduction reaction product, etc., were carried out, and the reaction activity, the n/i ratio, the yield of aldehydes and the hydrogenation ratio were obtained. The results are shown in Table 4.

EXAMPLES 13 TO 18

The hydroformylation reaction was carried out in the same manner as in Example 12, except that the ligand and the ligand/Rh ratio are as shown in Table 4. The results are shown in Table 4.

The structures of the phosphonite compounds used in Examples 12 to 18 are as follows.

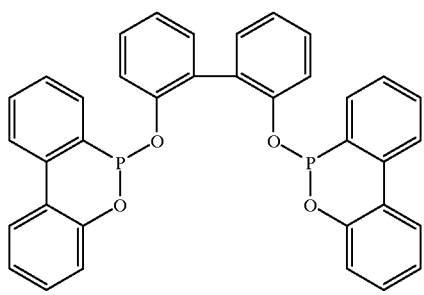

(80)

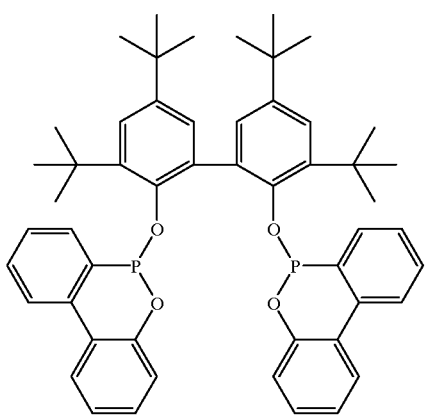

(81)

TABLE 4

| Ex. | Ligand | Ligand/Rh ratio (mol/mol) | Reaction time (hr.) | Activity *1 | Selectivity of a straight chain *2 (%) | Yield of aldehydes (%) | Hydrogenation ratio *3 (%) |
|---|---|---|---|---|---|---|---|
| 12 | (80) | 1.0 | 2.0 | 2.58 | 74.8 | 96.6 | 0.21 |
| 13 | (81) | 1.0 | 0.5 | >15.0 | 53.8 | 100.0 | 0.30 |
| 14 | (81) | 2.0 | 0.7 | 24.1 | 58.0 | 99.9 | 0.16 |
| 15 | (81) | 4.0 | 1.2 | 3.35 | 58.8 | 98.6 | 0.19 |
| 16 | (88) | 2.0 | 2.5 | 2.18 | 81.0 | 98.7 | 0.34 |
| 17 | (122) | 1.0 | 2.5 | 4.47 | 71.8 | 98.6 | 0.17 |
| 18 | (122) | 2.0 | 3.0 | 1.34 | 74.3 | 96.2 | 0.16 |

*1 Activity = mol-Aldehyde products/l·hr
*2 Selectivity of a straight chain = n-butyraldehyde/(n-butyraldehyde + i-butyraldehyde)
*3 Hydrogenation ratio = yield of produced propane (88)

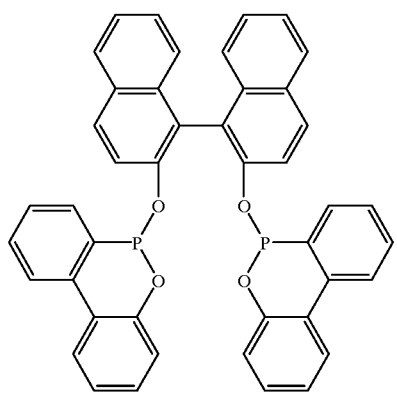

(122)

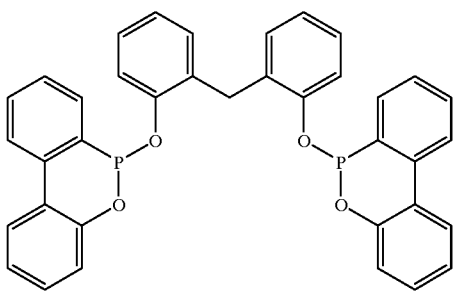

Reference Example 2
(Synthesis of Phosphonite Compound (80))

The interior of a four neck flask of 100 ml equipped with a stirring apparatus, a reflux condenser and a thermometer, was replaced by nitrogen, and 3.322 g (14.2 mmol) of 6-chloro-6H-dibenzo[c,e][1,2]oxaphosphorin and about 7 ml of THF were put therein, followed by stirring and cooling to 0° C. While keeping the stirring, a solution having 1.076 g (5.8 mmol) of 2,2'-dihydroxybiphenyl and 5.869 g (58 mmol) of triethylamine dissolved in about 6 ml of THF, was dropwisely added to the solution over a period of 10 minutes. After the dropwise addition, the stirring was carried out further for 3 hours. Then, by-product solid triethylammine hydrochloride was filtered off, the solvent was distilled off from the filtrate, to obtain a residual solid. Further, by silica gel column chromatography, 2.06 g (3.54 mmol) of phosphonite compound (80) as a white solid was isolated. The yield was 61.0%.

By using $^1$H, $^{13}$C and $^{31}$P nuclear magnetic resonance spectrophotometry (NMR; by using Unity 300 model manufactured by Barian), it was confirmed that the synthesized phosphonite compound (80) had a structure of the desired compound. By $^{31}$P nuclear magnetic resonance spectrophotometry, two resonance absorptions attributable to a diastereomer (a mixture of d,l-forms and a meso-form) were observed. The chemical shift values of each NMR are shown in Table 5.

TABLE 5

$^{31}$P NMR(δ, CDCl$_3$); 128.4, 126.9
$^1$H NMR(δ, CDCl$_3$; intensity, multiplicity, coupling constant (J in Hz));
7.84–7.76(4H, m), 7.46(2H, d, 5.7), 7.40(2H, d, 6.2),
7.36–7.10(8H, m), 7.06(2H, d, 7.4), 7.01(2H, d, 6.2),
6.92(2H, t, 4.5), 6.69(1H, d, 5.7), 6.65(1H, d, 5.7)

TABLE 5-continued $^{13}$C NMR(δ, CDCl$_3$, multiplicity, coupling constant (J in Hz) );
153.7(d, 6.0), 152.9(t, 3.0), 149.1(d, 15.0), 148.9(t, 7.5),
131.6(t, 8.0), 131.0(m), 130.2(s), 129.4(t, 7.5),
128.7(d, 16.7), 127.1(m), 124.9(d, 22.5), 123.8(s),
123.4(d 2.4), 123.2(3.9), 122.9(s), 122.5(t, 3.5), 120.6(t, 5.2), 120.4(s)

$^{31}$P NMR: Chemical shift values based on phosphoric acid
$^1$H NMR: Chemical shift values based on TMS
$^{13}$C NMR: Chemical shift values based on TMS By using $^1$H, $^{13}$C and $^{31}$P nuclear magnetic resonance spectrophotometry (NMR; by using Unity 300 model manufactured by Barian), it was confirmed that each of synthesized phosphonite compounds (mixtures of d,l-forms and a meso-form) used in Examples 13 to 18, had a structure of the desired compound. The chemical shift values of $^{31}$P NMR are shown in Table 6.

TABLE 6

| | $^{31}$P NMR(δ, CDCl$_3$); |
|---|---|
| (81) | 133.3, 132.5 |
| (88) | 130.1, 128.7, 127.3, 126.1 |
| (122) | 126.2, 125.8 |

$^{31}$P NMR: Chemical shift values based on phosphoric acid

EXAMPLE 19

Into an up and down stirring type stainless steel autoclave having an internal capacity of 200 ml, 55 ml of toluene as a solvent, 5 ml of heptane as an internal standard, and 39.4 mg of [Rh(OAc)(COD)]$_2$ and 4.0 mol per mol of rhodium of phosphonite compound (129) having the following structure as the ligand were charged under a nitrogen atmosphere, and then the autoclave was sealed. The interior of the autoclave was completely replaced by nitrogen gas, then the pressure was reduced, and 4.50 g of propylene was injected thereto. The temperature was raised to 70° C., and a synthesis gas (H$_2$/CO) was injected to the autoclave so that the total pressure became 10.0 atm, to initiate the reaction. The pressure in the autoclave to be used for the reaction was kept at a certain pressure until the completion of the reaction, by supplementing a synthesis gas through an automatic pressure regulator, and the reaction was carried out for 2.0 hours. After the completion of the reaction, the reactor was cooled to room temperature. The gas phase and the liquid phase in the autoclave were subjected to the analyses of the respective components by means of gas chromatography, quantitative analyses of the formed aldehydes, unreacted propylene, propane as a reduction reaction product, etc., were carried out, and the reaction activity, the selectivity of a straight chain, the yield of aldehydes and the hydrogenation ratio were obtained. The results are shown in Table 7.

EXAMPLE 20

The hydroformylation reaction was carried out in the same manner as in Example 19 except that phosphonite compound (132) having the following structure was used as the ligand, and the reaction time was 7 hours. The results are shown in Table 7.

The structures of the phosphonite compounds used in Examples 19 and 20 are as follows.

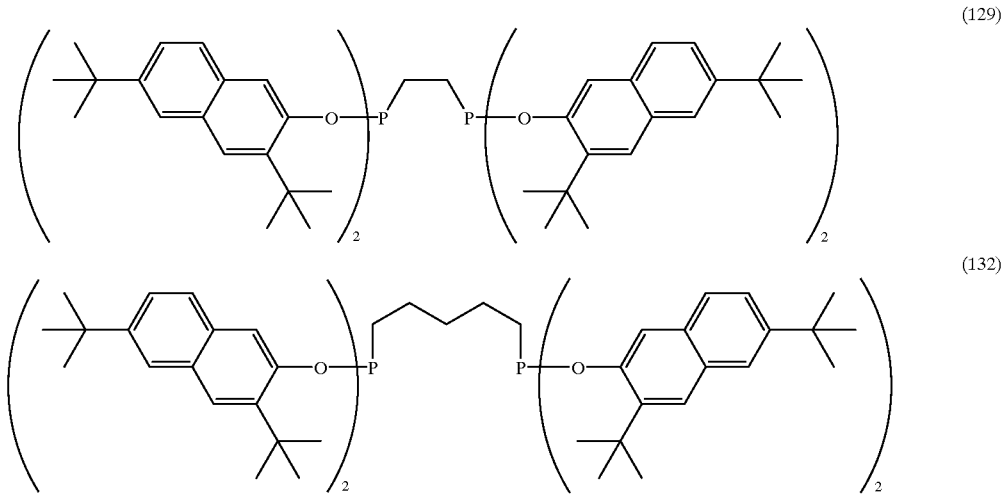

TABLE 4

| Ex. | Ligand | Ligand/Rh ratio (mol/mol) | Reaction time (hr.) | Activity *1 | Selectivity of a straight chain *2 (%) | Yield of aldehydes (%) | Hydrogenation ratio *3 (%) |
|---|---|---|---|---|---|---|---|
| 19 | (129) | 4.0 | 2.0 | 3.25 | 66.1 | 100 | 0.10 |
| 20 | (132) | 4.0 | 7.0 | 0.27 | 68.7 | 64.1 | 0.12 |

*1 Activity = mol-Aldehyde products/l·hr
*2 Selectivity of a straight chain = n-butyraldehyde/(n-butyraldehyde + i-butyraldehyde)
*3 Hydrogenation ratio = yield of produced propane The chemical shift values in NMR of the bidentate non-cyclic phosphonite compounds used in Examples 19 and 20, are shown in Table 8.

TABLE 8

| Ligand | $^{31}$P NMR Chemical shift value (?, CDCl$_3$) |
|---|---|
| (129) | 172.6 |
| (132) | 175.7 |

$^{31}$P: Chemical shift values based on phosphoric acid

What is claimed is:

1. A method for producing an aldehyde, comprising:

reacting an olefinic compound with carbon monoxide and hydrogen in the presence of a catalyst containing a metal of Group 8 to 10 and a trivalent organic phosphorus compound, thereby producing said aldehyde;

wherein said trivalent organic phosphorus compound is a phosphonite compound selected from the group consisting of a compound of formula (I), a compound of formula (II), a compound of formula (III), a compound of formula (IV) and a compound of formula (V);

wherein formula (I) is:

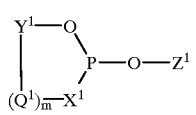

(I)

wherein
Z$^1$ is a substituted or unsubstituted hydrocarbon group;
each of X$^1$ and Y$^1$ is independently a substituted or unsubstituted bivalent hydrocarbon group;
Q$^1$ is a substituted or unsubstituted methylene group; and
m is 0 or a positive integer;

wherein formula (II) is:

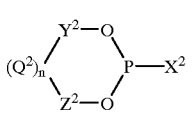

(II)

wherein
X$^2$ is a substituted or unsubstituted hydrocarbon group;
each of Y$^2$ and Z$^2$ is independently a substituted or unsubstituted bivalent hydrocarbon group;
Q$^2$ is a substituted or unsubstituted methylene group; and
n is 0 or a positive integer;

wherein formula (III) is:

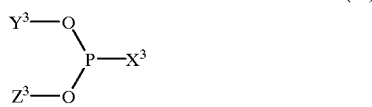

(III)

wherein
$X^3$ is a substituted or unsubstituted hydrocarbon group; and each of $Y^3$ and $Z^3$ is a substituted or unsubstituted aromatic hydrocarbon group;

wherein formula (IV) is:

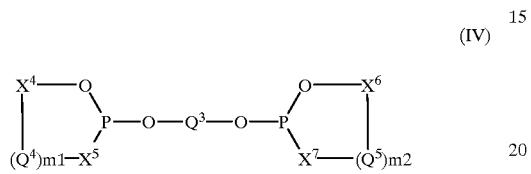

(IV)

wherein
each of $X^4$, $X^5$, $X^6$ and $X^7$ is independently a substituted or unsubstituted bivalent hydrocarbon group; $Q^3$ is a substituted or unsubstituted bivalent hydrocarbon group;
each of $Q^4$ and $Q^5$ is a substituted or unsubstituted methylene group; and each of m1 and m2 is 0 or a positive integer; and wherein formula (V) is:

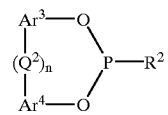

(V)

wherein
each of $X^8$, $X^9$, $X^{10}$ and $X^{11}$ is a substituted or unsubstituted hydrocarbon group; and
$Q^6$ is a bivalent organic group.

2. The method according to claim 1, wherein said phosphonite compound is represented by formula (I).

3. The method according to claim 2, wherein said phosphonite compound is represented by formula (I'):

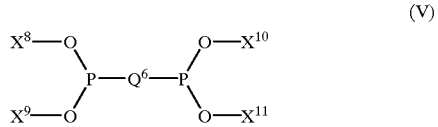

(I')

wherein
$R^1$ is a substituted or unsubstituted hydrocarbon group;
each of $Ar^1$ and $Ar^2$ is independently a substituted or unsubstituted bivalent aromatic hydrocarbon group;
$Q^1$ is a substituted or unsubstituted methylene group; and m is 0 or a positive integer.

4. The method according to claim 3, wherein m is 0 in said phosphonite compound of formula (I').

5. The method according to claim 3, wherein each of $Ar^1$ and $Ar^2$ is independently a substituted or unsubstituted phenylene group in said phosphonite compound of formula (I').

6. The method according to claim 3, wherein $R^1$ is a $C_{6-30}$ aryl group in said phosphonite compound of formula (I').

7. The method according to claim 3, wherein m is 0;
each of $Ar^1$ and $Ar^2$ is independently a substituted or unsubstituted phenylene group; and
$R^1$ is a $C_{6-30}$ aryl group in said phosphonite compound of formula (I').

8. The method according to claim 1, wherein said phosphonite compound is represented by formula (II).

9. The method according to claim 8, wherein said phosphonite compound is represented by formula (II'):

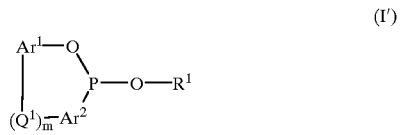

(II')

wherein
$R^2$ is a substituted or unsubstituted hydrocarbon group;
each of $Ar^3$ and $Ar^4$ is a substituted or unsubstituted bivalent aromatic hydrocarbon group;
$Q^2$ is a substituted or unsubstituted methylene group; and
n is 0 or a positive integer.

10. The method according to claim 9, wherein $R^2$ is a substituted or unsubstituted phenyl group or naphthyl group in said phosphonite compound of formula (II').

11. The method according to claim 9, wherein n is 0 or 1 in said phosphonite compound of formula (II').

12. The method according to claim 9, wherein each of $Ar^3$ and $Ar^4$ is a substituted or unsubstituted $C_{6-30}$ bivalent arylene group in said phosphonite compound of formula (II').

13. The method according to claim 9, wherein n is 0 or 1, each of $Ar^3$ and $Ar^4$ is a substituted or unsubstituted $C_{6-30}$ bivalent arylene group, and $R^2$ is a substituted or unsubstituted phenyl group or naphthyl group in said phosphonite compound of formula (II').

14. The method according to claim 1, wherein said phosphonite compound is represented by formula (III).

15. The method according to claim 14, wherein each of $Y^3$ and $Z^3$ is a substituted or unsubstituted $C_{6-30}$ aryl group in said phosphonite compound of formula (III).

16. The method according to claim 15, wherein each of $Y^3$ and $Z^3$ is a substituted or unsubstituted phenyl group or naphthyl group in said phosphonite compound of formula (III).

17. The method according to claim 14, wherein at least one of $Y^3$ and $Z^3$ is aromatic hydrocarbon having a substituent in said phosphonite compound of formula (III).

18. The method according to claim 14, wherein $X^3$ is a substituted or unsubstituted phenyl group in said phosphonite compound of formula (III).

19. The method according to claim 14, wherein each of $Y^3$ and $Z^3$ is a substituted or unsubstituted phenyl group or naphthyl group, and $X^3$ is a substituted or unsubstituted phenyl group in said phosphonite compound of formula (III).

20. The method according to claim 1, wherein said phosphonite compound is represented by formula (IV).

21. The method according to claim 20, wherein said phosphonite compound is represented by formula (IV'):

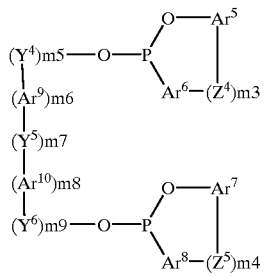

(IV')

wherein
each of $Ar^5$, $Ar^6$, $Ar^7$, $Ar^8$, $Ar^9$ and $Ar^{10}$ is independently a substituted or unsubstituted bivalent aromatic hydrocarbon group;

each of $Y^4$, $Y^5$ and $Y^6$ is independently a substituted or unsubstituted bivalent hydrocarbon group;

each of $Z^4$ and $Z^5$ is a substituted or unsubstituted methylene group; and each of m3, m4, m5, m6, m7, m8 and m9 is independently 0 or a positive integer.

22. The method according to claim 21, wherein each of $Ar^5$ to $Ar^{10}$ is independently a substituted or unsubstituted $C_{6-30}$ bivalent arylene group in said phosphonite compound of formula (IV').

23. The method according to claim 22, wherein each of $Ar^5$ to $Ar^{10}$ is independently a substituted or unsubstituted phenylene group or naphthylene group in said phosphonite compound of formula (IV').

24. The method according to claim 21, wherein $Z^4$ or $Z^5$ is a substituted or unsubstituted methylene group in said phosphonite compound of formula (IV').

25. The method according to claim 21, wherein both m3 and m4 are 0 in said phosphonite compound of formula (IV').

26. The method according to claim 21, wherein each of $Ar^5$ to $Ar^{10}$ is independently a substituted or unsubstituted phenylene group or naphthylene group, $Z^4$ or $Z^5$ is a substituted or unsubstituted methylene group, and both m3 and m4 are 0 in said phosphonite compound of formula (IV').

27. The method according to claim 1, wherein said phosphonite compound is represented by formula (V).

28. The method according to claim 27, wherein said phosphonite compound is represented by formula (V'):

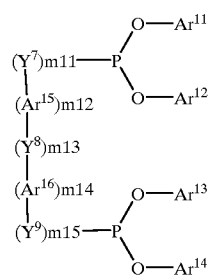

(V')

wherein
each of $Ar^{11}$, $Ar^{12}$, $Ar^{13}$ and $Ar^{14}$ is a substituted or unsubstituted aromatic hydrocarbon group;

each of $Ar^{15}$ and $Ar^{16}$ is a substituted or unsubstituted bivalent aromatic hydrocarbon group;

each of $Y^7$, $Y^8$ and $Y^9$ is a substituted or unsubstituted bivalent organic group which is not an aromatic hydrocarbon group; and each of m11, m12, m13, m14 and m15 is 0 or a positive integer.

29. The method according to claim 28, wherein each of $Ar^{11}$ and $Ar^{14}$ is a substituted or unsubstituted $C_{6-30}$ aryl group, and each of $Ar^{15}$ and $Ar^{16}$ is a substituted or unsubstituted $C_{6-30}$ arylene group in said phosphonite compound of formula (V').

30. The method according to claim 29, wherein each of $Ar^{11}$ to $Ar^{14}$ is a substituted or unsubstituted phenylene group or naphthylene group in said phosphonite compound of formula (V').

31. The method according to claim 28, wherein each of m11 to m15 is 0 or 1 in said phosphonite compound of formula (V').

32. The method according to claim 28, wherein each of $Y^7$ to $Y^9$ is one selected from the group consisting of a substituted or unsubstituted $C_{1-5}$ alkylene group, a carbonyl group, an imino group, a carbonylimino group, a substituted or unsubstituted sulfur atom, and a substituted or unsubstituted silylene group in said phosphonite compound of formula (V').

33. The method according to claim 28, wherein each of $Ar^{11}$ to $Ar^{14}$ is a substituted or unsubstituted phenylene group or naphthylene group, each of m11 to m15 is 0 or 1, and each of $Y^7$ to $Y^9$ is selected from the group consisting of a substituted or unsubstituted $C_{1-5}$ alkylene group, a carbonyl group, an imino group, a carbonylimino group, a substituted or unsubstituted sulfur atom, and a substituted or unsubstituted silylene group in said phosphonite compound of formula (V').

34. The method according to claim 1, wherein said reacting is carried out in a homogeneous system.

35. The method according to claim 1, wherein said reacting is carried out at a reaction temperature of from 50 to 150° C. and at a reaction pressure of from 5 to 50 atm.

36. The method according to claim 1, wherein an amount of said phosphonite compound is within a range of from 0.3 to 20 mol per mol of said metal of Group 8 to 10.

37. The method according to claim 1, wherein said metal of Group 8 to 10 is rhodium.

38. The method according to claim 1, wherein said olefinic compound is propylene.

* * * * *